US012566169B2

(12) United States Patent
Petroski et al.

(10) Patent No.: US 12,566,169 B2
(45) Date of Patent: *Mar. 3, 2026

(54) SOIL ANALYSIS COMPOSITIONS AND METHODS

(71) Applicant: Precision Planting LLC, Tremont, IL (US)

(72) Inventors: Richard Petroski, Tremont, IL (US); Rachel Nelson, Tremont, IL (US)

(73) Assignee: Precision Planting LLC, Tremont, IL (US)

( * ) Notice: Subject to any disclaimer, the term of this patent is extended or adjusted under 35 U.S.C. 154(b) by 559 days.

This patent is subject to a terminal disclaimer.

(21) Appl. No.: 18/004,405

(22) PCT Filed: May 20, 2021

(86) PCT No.: PCT/IB2021/054352
§ 371 (c)(1),
(2) Date: Jan. 5, 2023

(87) PCT Pub. No.: WO2022/013631
PCT Pub. Date: Jan. 20, 2022

(65) Prior Publication Data
US 2023/0266289 A1 Aug. 24, 2023

Related U.S. Application Data

(60) Provisional application No. 63/076,977, filed on Sep. 11, 2020, provisional application No. 63/052,341, (Continued)

(51) Int. Cl.
*G01N 33/24* (2006.01)
*G01N 1/38* (2006.01)
(Continued)

(52) U.S. Cl.
CPC .............. *G01N 33/24* (2013.01); *G01N 1/38* (2013.01); *G01N 1/4077* (2013.01);
(Continued)

(58) Field of Classification Search
None
See application file for complete search history.

(56) References Cited

U.S. PATENT DOCUMENTS 3,934,977 A 1/1976 Clever
5,482,866 A 1/1996 Denton
(Continued)

FOREIGN PATENT DOCUMENTS

CN 201373867 Y 12/2009
CN 108414463 A 8/2018
(Continued)

OTHER PUBLICATIONS

UK Intellectual Property Office, Search Report for related UK Application No. GB2011707.3, dated Jan. 18, 2021, 3 pages.
(Continued)

*Primary Examiner* — Lore R Jarrett

(57) ABSTRACT

Described herein is a method of analyzing nutrient content in soil, the method comprising a) obtaining a soil sample, b) adding a liquid to the soil sample to form a soil slurry, c) flowing the soil slurry through a filter, whereby the filter is oriented such that the soil slurry flows downward through the filter at least partially under the effects of gravity, d) blending a reagent composition with the soil slurry to form a soil mixture, and e) measuring an absorbance of the soil mixture.

19 Claims, 3 Drawing Sheets

Related U.S. Application Data filed on Jul. 15, 2020, provisional application No. 63/052,356, filed on Jul. 15, 2020, provisional application No. 63/052,405, filed on Jul. 15, 2020, provisional application No. 63/052,414, filed on Jul. 15, 2020, provisional application No. 63/052,334, filed on Jul. 15, 2020, provisional application No. 63/052,410, filed on Jul. 15, 2020, provisional application No. 63/052,399, filed on Jul. 15, 2020, provisional application No. 63/052,345, filed on Jul. 15, 2020, provisional application No. 63/052,395, filed on Jul. 15, 2020, provisional application No. 63/052,070, filed on Jul. 15, 2020, provisional application No. 63/052,406, filed on Jul. 15, 2020.

(51) Int. Cl.

| | |
|---|---|
| *G01N 1/40* | (2006.01) |
| *G01N 21/31* | (2006.01) |
| *G01N 21/65* | (2006.01) |
| *G01N 21/77* | (2006.01) |
| *G01N 21/80* | (2006.01) |
| *G01N 31/22* | (2006.01) |

(52) U.S. Cl.
CPC ........... *G01N 21/658* (2013.01); *G01N 21/77* (2013.01); *G01N 21/80* (2013.01); *G01N 31/22* (2013.01); *G01N 31/221* (2013.01); *G01N 2001/383* (2013.01); *G01N 2001/4088* (2013.01); *G01N 21/31* (2013.01); *G01N 2021/7763* (2013.01); *G01N 2021/7783* (2013.01); *G01N 33/245* (2024.05)

(56) References Cited

U.S. PATENT DOCUMENTS

| | | | |
|---|---|---|---|
| 5,526,705 A | 6/1996 | Skotnikov et al. | |
| 8,144,319 B2 | 3/2012 | Preiner et al. | |
| 8,477,295 B2 | 7/2013 | Preiner et al. | |
| 9,291,545 B1 | 3/2016 | White | |
| 9,478,590 B2 | 10/2016 | Lee | |
| 9,739,693 B2 | 8/2017 | White et al. | |
| 10,168,260 B2 | 1/2019 | White et al. | |
| 12,104,988 B2 | 10/2024 | Swanson et al. | |
| 2006/0088939 A1 | 4/2006 | Rajendram | |
| 2008/0227856 A1* | 9/2008 | Melker ................. | A01N 25/00 |
| | | | 504/298 |
| 2010/0283993 A1* | 11/2010 | Preiner ................. | G01N 21/00 |
| | | | 356/442 |
| 2012/0002192 A1* | 1/2012 | Preiner ................. | G01N 21/25 |
| | | | 356/51 |
| 2012/0014748 A1* | 1/2012 | Kubota ................ | A01C 21/007 |
| | | | 405/128.7 |
| 2012/0147368 A1 | 6/2012 | Preiner et al. | |
| 2013/0019664 A1 | 1/2013 | Preiner et al. | |
| 2013/0247655 A1 | 9/2013 | Preiner | |
| 2016/0018380 A1 | 1/2016 | Gerber-Siff | |
| 2016/0270289 A1 | 9/2016 | Schildroth et al. | |
| 2016/0274009 A1* | 9/2016 | White ...................... | G01N 1/38 |
| 2017/0322148 A1* | 11/2017 | Preiner ................. | G01N 33/24 |
| 2018/0037926 A1 | 2/2018 | Fitzpatrick | |
| 2018/0224419 A1* | 8/2018 | Gerber-Siff .......... | G01N 1/4077 |
| 2018/0364155 A1 | 12/2018 | Thompson | |
| 2019/0120737 A1 | 4/2019 | White | |
| 2020/0158630 A1 | 5/2020 | Preiner et al. | |
| 2021/0053048 A1 | 2/2021 | Swanson et al. | |
| 2021/0123936 A1 | 4/2021 | Swanson et al. | |
| 2021/0341442 A1 | 11/2021 | Petroski et al. | |

FOREIGN PATENT DOCUMENTS

| | | |
|---|---|---|
| JP | 58153166 | 9/1983 |
| JP | 2003262629 A | 9/2003 |
| KR | 100346642 B1 | 8/2002 |
| WO | 9604553 A1 | 2/1996 |
| WO | 2010129877 | 11/2010 |
| WO | 2019211683 A1 | 11/2019 |
| WO | 2020012369 A2 | 1/2020 |
| WO | 2020148640 A2 | 7/2020 |
| WO | 2020163971 A1 | 8/2020 |
| WO | 2022013626 A1 | 1/2022 |

OTHER PUBLICATIONS

European Patent Office, International Search Report related to International Patent Application No. PCT/IB2021/054352, mail date Aug. 9, 2021, 11 pages.
U.S. Appl. No. 18/002,735, filed Dec. 21, 2022.
U.S. Appl. No. 18/002,745, filed Dec. 23, 2022.
U.S. Appl. No. 18/003,270, filed Dec. 23, 2022.
U.S. Appl. No. 18/003,276, filed Dec. 23, 2022.
U.S. Appl. No. 18/004,351, filed Jan. 5, 2023.
U.S. Appl. No. 18/004,357, filed Jan. 5, 2023.
U.S. Appl. No. 18/004,389, filed Jan. 5, 2023.
U.S. Appl. No. 18/004,397, filed Jan. 5, 2023.
U.S. Appl. No. 18/004,415, filed Jan. 5, 2023.
U.S. Appl. No. 18/004,423, filed Jan. 5, 2023.
Van Der Ent et al. "Evaluating soil extraction methods for chemical characterisation of ultramafic soils in Kinabalu Park (Malaysia)", Journal of Geochemical Exploration vol. 196, Jan. 2019, pp. 235-246.

* cited by examiner

SOIL ANALYSIS COMPOSITIONS AND METHODS

CROSS REFERENCE TO RELATED APPLICATIONS

This application is a national stage entry of PCT/IB2021/054352, filed 20 May 2021, and which claims priority to U.S. Provisional Application Nos. 63/052,070, filed 15 Jul. 2020; 63/052,334, filed 15 Jul. 2020; 63/052,341, filed 15 Jul. 2020; 63/052,345, filed 15 Jul. 2020; 63/052,356, filed 15 Jul. 2020; 63/052,395, filed 15 Jul. 2020; 63/052,399, filed 15 Jul. 2020; 63/052,405, filed 15 Jul. 2020; 63/052,406, filed 15 Jul. 2020; 63/052,410, filed 15 Jul. 2020; 63/052,414, filed 15 Jul. 2020; and 63/076,977, filed 11 Sep. 2020, all of which are incorporated herein by reference in their entireties.

BACKGROUND

Soil analysis of agricultural fields allows a grower to know whether there are sufficient amounts of nutrients in the soil for planting. If one or more nutrients is deficient, then the nutrient can be added to soil. There are many standardized soil tests available today, such as measurement of pH with a pH meter and measurement of soil nutrients by atomic spectroscopy. These tests, however, were designed for laboratory testing, and they are not suitable for an on the go soil sampling system. It would be desirable to test soil samples on the go with soil tests that can provide results while in the field.

BRIEF SUMMARY

The present disclosure includes a method of analyzing potassium content in soil, the method comprising: a) obtaining a soil sample; b) adding a liquid to the soil sample to form a soil slurry; c) flowing the soil slurry through a filter to form a filtrate; d) blending a reagent composition with the filtrate to form a soil mixture; and e) flowing the soil mixture through an analysis tool along a flow direction whereby a potassium absorbance of the soil mixture is measured; and wherein the flow direction is oriented such that the soil mixture flows vertically.

In other embodiments, the present disclosure includes a method of analyzing magnesium content in soil, the method comprising: a) obtaining a soil sample; b) adding a liquid to the soil sample to form a soil slurry; c) flowing the soil slurry through a filter to form a filtrate; d) blending a reagent composition with the filtrate to form a soil mixture; and e) flowing the soil mixture through an analysis tool along a flow direction whereby a magnesium absorbance of the soil mixture is measured; and wherein the flow direction is oriented such that the soil mixture flows vertically.

In other embodiments, the present disclosure includes a method of analyzing calcium content in soil, the method comprising: a) obtaining a soil sample; b) adding a liquid to the soil sample to form a soil slurry; c) flowing the soil slurry through a filter to form a filtrate; d) blending a reagent composition with the filtrate to form a soil mixture; and e) flowing the soil mixture through an analysis tool along a flow direction whereby a calcium absorbance of the soil mixture is measured; and wherein the flow direction is oriented such that the soil mixture flows vertically.

In other embodiments, the present disclosure includes a method of analyzing phosphorus content in soil, the method comprising: a) obtaining a soil sample; b) adding a liquid to the soil sample to form a soil slurry; c) flowing the soil slurry through a filter to form a filtrate; d) blending a reagent composition with the filtrate to form a soil mixture; and e) flowing the soil mixture through an analysis tool along a flow direction whereby a phosphorus absorbance of the soil mixture is measured, wherein the flow direction is oriented such that the soil mixture flows vertically.

In other embodiments, the present disclosure includes a method of analyzing potassium content in soil, the method comprising: a) obtaining a soil sample; b) adding a liquid to the soil sample to form a soil slurry; c) flowing the soil slurry through a filter to form a filtrate; d) blending a reagent composition with the filtrate to form a soil mixture; and e) flowing the soil mixture through an analysis tool along a flow direction whereby a potassium absorbance of the soil mixture is measured; and wherein the soil mixture comprises a surfactant and the flow direction is substantially horizontal and orthogonal to the direction of gravity.

Other embodiments of the present disclosure include a method of analyzing magnesium content in soil, the method comprising: a) obtaining a soil sample; b) adding a liquid to the soil sample to form a soil slurry; c) flowing the soil slurry through a filter to form a filtrate; d) blending a reagent composition with the filtrate to form a soil mixture; and e) flowing the soil mixture through an analysis tool along a flow direction whereby a magnesium absorbance of the soil mixture is measured; and wherein soil mixture comprises a surfactant and the flow direction is substantially horizontal and orthogonal to the direction of gravity.

Other embodiments of the present disclosure include a method of analyzing calcium content in soil, the method comprising: a) obtaining a soil sample; b) adding a liquid to the soil sample to form a soil slurry; c) flowing the soil slurry through a filter to form a filtrate; d) blending a reagent composition with the filtrate to form a soil mixture; and e) flowing the soil mixture through an analysis tool along a flow direction whereby a calcium absorbance of the soil mixture is measured; and wherein soil mixture comprises a surfactant and the flow direction is substantially horizontal and orthogonal to the direction of gravity.

Other embodiments of the present disclosure include a method of analyzing phosphorus content in soil, the method comprising: a) obtaining a soil sample; b) adding a liquid to the soil sample to form a soil slurry; c) flowing the soil slurry through a filter to form a filtrate; d) blending a reagent composition with the filtrate to form a soil mixture; and e) flowing the soil mixture through an analysis tool along a flow direction whereby a phosphorus absorbance of the soil mixture is measured; wherein soil mixture comprises a surfactant and the flow direction is substantially horizontal and orthogonal to the direction of gravity.

Other embodiments of the present disclosure include a method of analyzing pH in soil, the method comprising: a) obtaining a soil sample; b) adding a liquid to the soil sample to form a soil slurry; c) flowing the soil slurry through a filter to form a filtrate; d) blending an indicator composition with the filtrate to form a soil mixture; and e) flowing the soil mixture through an analysis tool along a flow direction whereby a pH value of the soil mixture is measured; and wherein the flow direction is oriented such that the soil mixture flows vertically.

Other embodiments of the present disclosure include a method of analyzing pH in soil, the method comprising: a) obtaining a soil sample; b) adding a liquid to the soil sample to form a soil slurry; c) flowing the soil slurry through a filter to form a filtrate; d) blending an indicator composition with the filtrate to form a soil mixture; and e) flowing the soil mixture through an analysis tool along a flow direction whereby a pH value of the soil mixture is measured; and wherein soil mixture comprises a surfactant and the flow direction is substantially horizontal and orthogonal to the direction of gravity.

Other embodiments of the present disclosure include a method of analyzing buffer pH in soil, the method comprising: a) obtaining a soil sample; b) adding a liquid to the soil sample to form a soil slurry; c) flowing the soil slurry through a filter to form a filtrate; d) blending an indicator composition with the filtrate to form a soil mixture; and e) flowing the soil mixture through an analysis tool along a flow direction whereby a buffer pH value of the soil mixture is measured; and wherein the flow direction is oriented such that the soil mixture flows vertically.

Other embodiments of the present disclosure include a method of analyzing buffer pH in soil, the method comprising: a) obtaining a soil sample; b) adding a liquid to the soil sample to form a soil slurry; c) flowing the soil slurry through a filter to form a filtrate; d) blending an indicator composition with the filtrate to form a soil mixture; and e) flowing the soil mixture through an analysis tool along a flow direction whereby a pH value of the soil mixture is measured; and wherein soil mixture comprises a surfactant and the flow direction is substantially horizontal and orthogonal to the direction of gravity.

Accordingly, the present invention is expressly not limited to use with soil sampling at any particular location but can be used at any location.

BRIEF DESCRIPTION OF THE DRAWINGS

The present invention will become more fully understood from the detailed description and the accompanying drawings, wherein.

DETAILED DESCRIPTION

Figure 1:
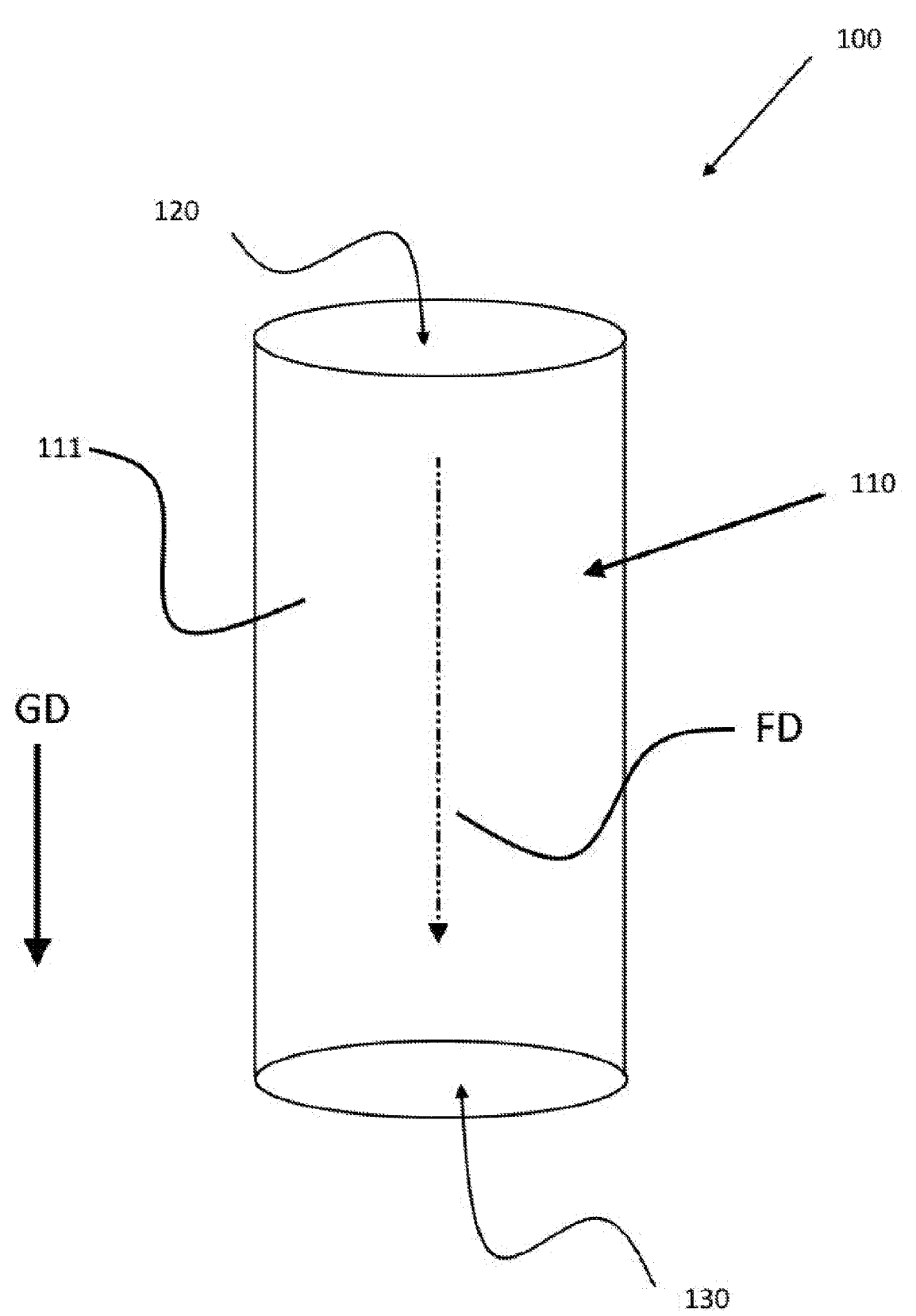
FIG. 1 is a schematic representation of a filtration-based analysis system according to one embodiment.

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

The description of illustrative embodiments according to principles of the present disclosure is intended to be read in connection with the accompanying drawings, which are to be considered part of the entire written description. In the description of embodiments of the disclosure disclosed herein, any reference to direction or orientation is merely intended for convenience of description and is not intended in any way to limit the scope of the present disclosure. Relative terms such as "lower," "upper," "horizontal," "vertical," "above," "below," "up," "down," "top," and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such.

Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the disclosure are illustrated by reference to the exemplified embodiments. Accordingly, the disclosure expressly should not be limited to such exemplary embodiments illustrating some possible non-limiting combination of features that may exist alone or in other combinations of features; the scope of the disclosure being defined by the claims appended hereto.

Unless otherwise specified, all percentages and amounts expressed herein and elsewhere in the specification should be understood to refer to percentages by weight. The amounts given are based on the active weight of the material. According to the present application, the term "about" means+/−5% of the reference value. According to the present application, the term "substantially free" means less than about 0.1 wt. % based on the total of the referenced value.

The features and benefits of the disclosure are illustrated and described herein by reference to exemplary ("example") embodiments. This description of exemplary embodiments is intended to be read in connection with the accompanying drawings, which are to be considered part of the entire written description. Accordingly, the disclosure expressly should not be limited to such exemplary embodiments illustrating some possible non-limiting combination of features that may exist alone or in other combinations of features.

The compositions and methods described below can be used with on the go soil sampling systems, such as those described in PCT Publication No. WO2020/012369A2. Also, the tests and methods can be used in a laboratory. When used in on the go systems, it is desirable to obtain results in a short period of time (shorter than traditional laboratory testing) so that multiple samples can be tested while traversing the field. This allows a grower to adjust application rates of nutrients in real time.

As demonstrated by FIG. 1, a filtration-based analysis system 100 may be used in accordance with soil analysis. The filtration-based system 100 may comprise an analysis tool 110 having housing 111 having an input 120 and an output 130. The input 120 may be fluidly coupled to the output 130, whereby one or more filtration elements are positioned there-between. The filtration-based analysis system 100 may be configured such that a fluid may be introduced to the housing 111 of the analysis tool 110 via the input 120 and pass through the housing 111 along a flow direction FD to reach the output 130, whereby the fluid may pas through the one or more filtration elements located inside of the housing 111 between the input 120 and the output 130. As the liquid flows along the flow direction FD, the liquid passes through the filtration element and is subjected to a filtration step—as discussed in greater detail herein.

After the filtration step, the liquid may further be subject to a chemical analysis as the liquid flows along the flow direction FD from the input 120 to the output 130—as discussed in greater detail herein.

In a non-limiting embodiment, the housing 111 may be formed of a polymeric material. Non-limiting examples of polymeric material may include one or more of an acrylic polymer, polycarbonate, and polyurethane. In a non-limiting embodiment, the housing 111 may be formed of an inorganic material. Non-limiting examples of inorganic material may include one or more of glass—such as borosilicate glass.

According to the embodiment demonstrated by FIG. 1, the analysis tool 110 may be configured within the filtration-based analysis system 100 such that flow direction FD extends along the gravitational direction GD. The term "gravitational direction" refers to the natural downward direction of earth's gravity. According to this embodiment, the filtration-based analysis system 100 of FIG. 1 may be configured such that the liquid may pass between the input 120 and the output 130 under solely the effects of gravity.

In a non-limiting embodiment, the filtration-based analysis system 100 is shown in FIG. 1 to be configured such that flow direction FD extends substantially parallel to the gravitational direction GD. The term "substantially parallel" refers to an angle between two lines that is 0°±2°. In some embodiments, the filtration-based analysis system 100 may be configured such that flow direction FD extends parallel to the gravitational direction GD.

Although not shown in FIG. 1, the filtration-based analysis system 100 may also be configured such that the flow direction FD and the gravitational direction GD are oriented at a first oblique angle so long as the liquid may pass between the input 120 and the output 130 under solely the effects of gravity. In a non-limiting embodiment, the first oblique angle between the flow direction FD and the gravitational direction GD may range from about 10 to about 450—including all angles and sub-ranges there-between.

According to the present disclosure, the filtration-based analysis system 100 may be free of a centrifuge.

Figure 3:
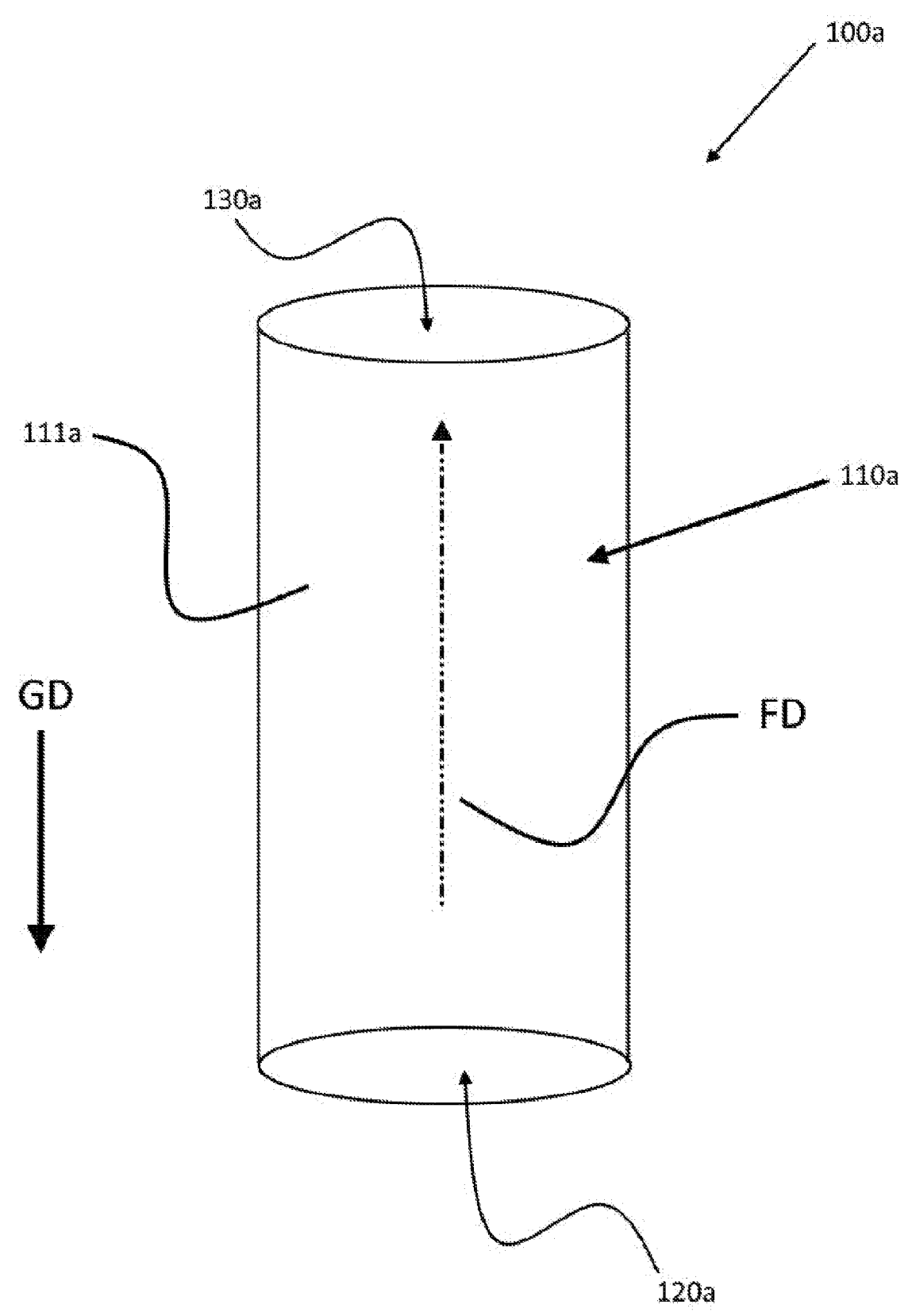
FIG. 3 is a schematic representation of a filtration-based analysis system according to another embodiment.

As demonstrated by FIG. 3, a filtration-based analysis system 100a may be used in accordance with soil analysis. The filtration-based system 100a may comprise an analysis tool 110a having housing 111a having an input 120a and an output 130a. The input 120a may be fluidly coupled to the output 130a, whereby one or more filtration elements are positioned there-between. The filtration-based analysis system 100a may be configured such that a fluid may be introduced to the housing 111a of the analysis tool 110a via the input 120a and pass through the housing 111a along a flow direction FD to reach the output 130a, whereby the fluid may pass through the one or more filtration elements located inside of the housing 111a between the input 120a and the output 130a. As the liquid flows along the flow direction FD, the liquid passes through the filtration element and is subjected to a filtration step—as discussed in greater detail herein.

After the filtration step, the liquid may further be subject to a chemical analysis as the liquid flows along the flow direction FD from the input 120a to the output 130a—as discussed in greater detail herein.

In a non-limiting embodiment, the housing 111a may be formed of a polymeric material. Non-limiting examples of polymeric material may include one or more of an acrylic polymer, polycarbonate, and polyurethane. In a non-limiting embodiment, the housing 111a may be formed of an inorganic material. Non-limiting examples of inorganic material may include one or more of glass—such as borosilicate glass.

According to the embodiment demonstrated by FIG. 3, the analysis tool 110a may be configured within the filtration-based analysis system 100a such that flow direction FD extends along the gravitational direction GD. According to this embodiment, the filtration-based analysis system 100a of FIG. 3 may be configured such that the liquid may pass between the input 120a and the output 130a against the effects of gravity. According to this embodiment, the flow direction FD of the liquid may be facilitated by a pump that applies pressure to the liquid which overcomes the force of gravity to allow the liquid to flow along the FD and pass between the input 120a and the output 130a against the effects of gravity.

In a non-limiting embodiment, the filtration-based analysis system 100a is shown in FIG. 3 to be configured such that flow direction FD extends substantially parallel to the gravitational direction GD. The term "substantially parallel" refers to an angle between two lines that is 0°±2°. In some embodiments, the filtration-based analysis system 100a may be configured such that flow direction FD extends parallel to the gravitational direction GD.

Although not shown in FIG. 3, the filtration-based analysis system 100a may also be configured such that the flow direction FD and the gravitational direction GD are oriented at a third oblique angle ranging from about 10 to about 450—including all angles and sub-ranges there-between.

Figure 2:
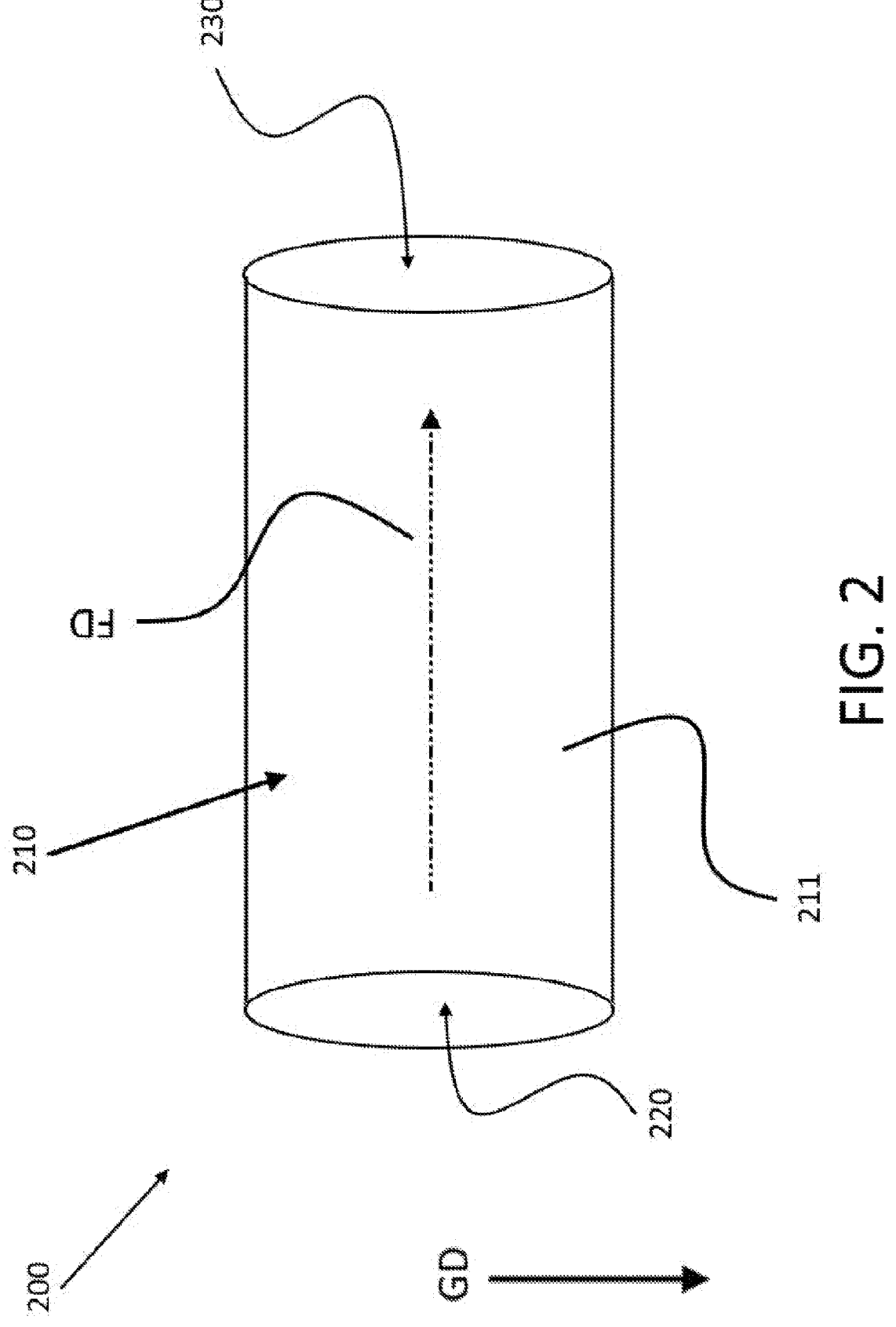
FIG. 2 is a schematic representation of a filtration-based analysis system according to another embodiment.

As demonstrated by FIG. 2, a filtration-based analysis system 200 may be used in accordance with soil analysis. The filtration-based analysis system 200 may comprise an analysis tool 210 having housing 211 having an input 220 and an output 230. The input 220 may be fluidly coupled to the output 230, whereby one or more filtration elements are positioned there-between. The filtration-based analysis system 200 may be configured such that a fluid may be introduced to the housing 211 of the analysis tool 210 via the input 220 and pass through the housing 211 along a flow direction FD to reach the output 230, whereby the fluid passes through the one or more filtration elements located inside of the housing 211 between the input 220 and the output 230. As the liquid flows along the flow direction FD, the liquid passes through the filtration element and is subjected to a filtration step—as discussed in greater detail herein.

After the filtration step, the liquid may further be subject to a chemical analysis as the liquid flows along the flow direction FD from the input 220 to the output 230—as discussed in greater detail herein.

According to the embodiment demonstrated by FIG. 2, the analysis tool 210 may be configured within the filtration-based analysis system 200 such that flow direction FD extends substantially orthogonal to the gravitational direction GD. The term "substantially orthogonal" refers to an angle between two lines that is 900° 2°. According to this embodiment, the filtration-based analysis system 200 of FIG. 2 may be configured such that at least a portion of the liquid may not pass between the input 220 and the output 230 under solely the effects of gravity during the filtration step.

In a non-limiting embodiment, the filtration-based analysis system 200 is shown in FIG. 2 to be configured such that flow direction FD extends orthogonal to the gravitational direction GD. Although not shown in FIG. 2, the filtration-based analysis system 200 of FIG. 2 may also be configured such that the flow direction FD and the gravitational direction GD are oriented at a second oblique angle so long as at least a portion of the liquid may not pass between the input 220 and the output 230 under solely the effects of gravity. In a non-limiting embodiment, the second oblique angle between the flow direction FD and the gravitational direction GD may range from about 45° to about 90°—including all angles and sub-ranges there-between.

According to the present disclosure, the filtration-based analysis system 200 may be free of a centrifuge.

The soil analysis may be performed to determine an elemental content of a soil sample. Non-limiting examples of element content include potassium, magnesium, calcium, and phosphorus.

The soil analysis may be performed by collecting a soil extract or soil sample. The soil sample may be taken directly from the ground can be used without first drying and grinding. The soil sample may be mixed in a 1:2 weight to 1:3 weight ratio with a liquid, such as water, to form a slurry. In other embodiments, a weight ratio of soil to liquid is 1:1 to 1:5—including all ratios and sub-ranges there-between.

In some embodiments, the slurry may be mixed with a flocculating agent. Non-limiting examples of flocculating agent include, but are not limited to, calcium chloride, polyacrylamide, cationic polyacrylamide, anionic polyacrylamide, polydiallyldimethyl ammonium chloride (PDADMAC), epichlorohydin/dimethylamine copolymer (ECH/DMA), chitosan, and polyaluminum chlorides. In one embodiment, the flocculating agent may be calcium chloride. In another embodiment, the flocculating agent may be a combination of polyacrylamide and calcium chloride. In another embodiment, the flocculating agent may be polyacrylamide. The amount of flocculating agent varies on the type of flocculating agent chosen.

The flocculating agent amount may be chosen to remove organic materials and/or reduce or eliminate cloudiness. In one embodiment, a 0.017M $CaCl_2 \cdot 2H_2O$ solution is used.

Alternatively, the anhydride or other hydrates of calcium chloride may be used. In one embodiment, a molar concentration for calcium chloride is 0.005M to 0.1M—including all concentrations and sub-ranges there-between.

The soil slurry may be mixed with the flocculating agent in a volume ratio of 9:1 soil slurry:flocculating agent. In other embodiments, a volume ratio of slurry to flocculating agent may be 1:1 to 10:1—including all ratios and sub-ranges there-between. In another embodiment, the calcium chloride solution can be replaced with a 0.025 weight % polyacrylamide solution. In one embodiment, the polyacrylamide can have a weight average molecular weight of 5,000,000 to 6,000,000 (CAS 9003-05-8). Other flocculating agents can be used in amounts that provide the same amount of flocculation as the above calcium chloride or polyacrylamide solutions. The soil slurry and flocculating agent are centrifuged to form the soil extract.

In a non-limiting embodiment, soil samples may be prepared as for typical laboratory testing by drying, crushing, and filtering to less than 2 mm particle size. Multiple samples are prepared to provide a sufficient number to generate a calibration curve.

Potassium Analysis

According to an embodiment of the present disclosure, potassium may be tested according to the following methodologies. A soil sample may be obtained and blended with liquid to create the soil slurry. The soil slurry may then flow through the filter element to create a filtrate, whereby one or more reagent may be added to the filtrate to create a mixture.

The soil mixture may then be analyzed for potassium content by absorbance that may be read via a spectrophotometer at a wavelength ranging from 380 nm to 550 nm—preferably 410 nm to about 510 nm—including all wavelengths and sub-ranges there-between.

In some embodiments, the potassium content analysis may occur inside of the analysis tool 110 and as the soil mixture flows along the vertical FD, whereby the vertical FD is substantially parallel to gravitational direction GD such that the soil mixture flows downward at least partially under the effects of gravity. In some embodiments, the potassium content analysis may occur inside of the analysis tool 110*a* and as the soil mixture flows along the vertical FD, whereby the vertical FD is substantially parallel to gravitational direction GD such that the soil mixture flows upward against the effects of gravity.

In alternative embodiments, the potassium content analysis may occur inside of the analysis tool 210 and as the soil mixture flows along the horizontal FD, whereby the horizontal FD is substantially orthogonal to the gravitational direction GD and the soil slurry flows horizontally through the analysis tool 210.

According to embodiments of the potassium content analysis using the vertical FD and horizontal FD, a surfactant may be added to the soil slurry. It has been surprisingly discovered that the addition of an anionic surfactant provides an unexpected improvement in optical clarity that enhances the spectrophotometer potassium content analysis while other non-anionic surfactants fail to provide such improved optical properties. Non-limiting examples of anionic surfactant include sodium laurate phosphate, sodium laurate sulfate, and sodium dodecyl sulfate. The surfactant of this embodiment may be substantially free of non-ionic compounds. The surfactant of this embodiment may be substantially free of cationic compounds.

It has also been surprisingly discovered that for the embodiments of the potassium content analysis that utilize a vertical FD, the soil slurry may also be substantially free of surfactant and still achieve the desire optical clarity while the same optical clarity is not achieved in the absence of such surfactants in the horizontal FD.

According to the embodiments directed to the potassium analysis, non-limiting examples of reagents include lithium hydroxide, sodium hydroxide, tetraphenylborate in sodium hydroxide, and sodium tetraborate decahydate in glycerol.

The reagents may comprise a first reagent that includes lithium hydroxide is present in a concentration of about 0.01 M to about 0.3 M—including all concentrations and sub-ranges there-between. The reagents may comprise a second reagent that includes tetraphenylborate in a concentration of 0.5% to 4%—including all concentrations and sub-ranges there-between—and NaOH in a concentration of about 0.01M to about 0.15M—including all concentrations and sub-ranges there-between. The reagents may comprise a third reagent that includes sodium tetraborate decahydrate in a concentration ranging from about 0.0001M to about 0.05M—including all concentrations and sub-ranges there-between—in about 1% to about 5% aqueous glycerol—including all concentrations and sub-ranges there-between.

An extractant may be blended with the soil slurry. Non-limiting examples of extractant include nitric acid. The extractant may comprise nitric acid in a concentration ranging from about 0.01M to about 0.2M—including all concentrations and sub-ranges there-between.

According to this embodiment, the soil sample may be prepared by mixing the filtrate with the first reagent, subsequently mixing with the second reagent, subsequently mixing 0.8 mL of the third reagent, and subsequently performing the absorbance reading.

According to this embodiment, the soil slurry and soil mixture may not be subjected to a centrifuge force before performing the potassium absorbance reading.

Magnesium Analysis

According to an embodiment of the present disclosure, magnesium analysis may be performed according to the following methodologies. A soil sample may be obtained and blended with liquid to create the soil slurry. The soil slurry may then flow through the filter element to create a filtrate, whereby one or more reagent may be added to the filtrate to create a mixture.

The soil mixture may then be analyzed for magnesium content by absorbance that may be read via a spectrophotometer at a wavelength ranging from 600 nm to 690 nm. In some embodiments, the soil mixture may then be analyzed for magnesium content by absorbance that may be read via a spectrophotometer at a wavelength ranging from 600 nm to 635 nm—including all wavelengths and sub-ranges therebetween—preferably about 615 nm. In some embodiments, the soil mixture may then be analyzed for magnesium content by absorbance that may be read via a spectrophotometer at a wavelength ranging from 650 nm to 690 nm—including all wavelengths and sub-ranges there-between—preferably about 669 nm.

In some embodiments, the magnesium content analysis may occur inside of the analysis tool 110 and as the soil mixture flows along the vertical FD, whereby the vertical FD is substantially parallel to gravitational direction GD such that the soil mixture flows downward at least partially under the effects of gravity. In some embodiments, the magnesium content analysis may occur inside of the analysis tool 110a and as the soil mixture flows along the vertical FD, whereby the vertical FD is substantially parallel to gravitational direction GD such that the soil mixture flows upward against the effects of gravity.

In alternative embodiments, the magnesium content analysis may occur inside of the analysis tool 210 and as the soil mixture flows along the horizontal FD, whereby the horizontal FD is substantially orthogonal to the gravitational direction GD and the soil slurry flows horizontally through the analysis tool 210.

According to embodiments of the magnesium content analysis using the vertical FD and horizontal FD, the soil slurry may comprise a surfactant. It has been surprisingly discovered that the addition of a non-ionic surfactant provides an unexpected improvement in optical clarity that enhances the spectrophotometer magnesium content analysis while ionic surfactants fail to provide such improved optical properties. Non-limiting examples of non-ionic surfactant include 4-nonylphenyl polyethylene glycol, poly (ethylene glycol)(18) tridecylether, and mixtures thereof. The surfactant of this embodiment may be substantially free of ionic surfactant. The surfactant of this embodiment may be substantially free of anionic surfactant. The surfactant of this embodiment may be substantially free of cationic surfactant.

It has also been surprisingly discovered that for the embodiments of the magnesium content analysis that utilize a vertical FD, the soil slurry may also be substantially free of surfactant and still achieve the desire optical clarity while the same optical clarity is not achieved in the absence of such surfactants in the horizontal FD.

According to the embodiments directed to the magnesium analysis, non-limiting examples of reagents include tetrabutylammonium hydroxide in boric acid as well as chlorophosphonazo III.

The reagents may comprise a first reagent that includes tetrabutylammonium hydroxide in an concentration of about 0.05% to about 0.3%—including all sub-ranges and concentrations there-between—and boric acid in a concentration of about 0.01% to about 0.1%—including all sub-ranges and concentrations there-between. In some embodiments, the reagents may comprise a second reagent that includes chlorophosphonazo III in a concentration of about 0.5 mg to about 1.5 mg per mL of water—including all concentrations and sub-ranges there-between.

The magnesium analysis may further include the addition of an extractant, which may be blended with the soil slurry. Non-limiting examples ofextractant include ammonium acetate. The extractant may comprise ammonium acetate in a concentration ranging from about 0.5M to about 1.5M—including all concentrations and sub-ranges there-between.

According to this embodiment, the soil sample may be prepared by mixing the filtrate with the first reagent and subsequently mixing the second reagent, and subsequently performing the absorbance reading.

According to this embodiment, the soil slurry and soil mixture may not be subjected to a centrifuge force before performing the magnesium absorbance reading.

Calcium Analysis

According to an embodiment of the present disclosure, calcium may be tested according to the following methodology. A soil sample may be obtained and blended with liquid to create the soil slurry. The soil slurry may then flow through the filter element to create a filtrate, whereby one or more reagent may be added to the filtrate to create a mixture.

The soil mixture may then be analyzed for calcium content by absorbance that may be read via a spectrophotometer at a wavelength ranging from 600 nm to 690 nm. In some embodiments, the soil mixture may then be analyzed for calcium content by absorbance that may be read via a spectrophotometer at a wavelength ranging from 600 nm to 635 nm—including all wavelengths and sub-ranges there-between—preferably about 615 nm.

In some embodiments, the calcium content analysis may occur inside of the analysis tool 110 and as the soil mixture flows along the vertical FD, whereby the vertical FD is substantially parallel to gravitational direction GD such that the soil mixture flows downward at least partially under the effects of gravity. In some embodiments, the calcium content analysis may occur inside of the analysis tool 110a and as the soil mixture flows along the vertical FD, whereby the vertical FD is substantially parallel to gravitational direction GD such that the soil mixture flows upward against the effects of gravity.

In alternative embodiments, the calcium content analysis may occur inside of the analysis tool 210 and as the soil mixture flows along the horizontal FD, whereby the horizontal FD is substantially orthogonal to the gravitational direction GD and the soil slurry flows horizontally through the analysis tool 210.

According to embodiments of the calcium content analysis using the vertical FD and horizontal FD, the soil slurry may comprise a surfactant. It has been surprisingly discovered that the addition of a non-ionic surfactant provides an unexpected improvement in optical clarity that enhances the spectrophotometer calcium content analysis while ionic surfactants fail to provide such improved optical properties. Non-limiting examples of non-ionic surfactant include 4-nonylphenyl polyethylene glycol, poly(ethylene glycol) (18) tridecylether, and mixtures thereof. The surfactant of this embodiment may be substantially free of ionic surfactant. The surfactant of this embodiment may be substantially free of anionic surfactant. The surfactant of this embodiment may be substantially free of cationic surfactant.

It has also been surprisingly discovered that for the embodiments of the calcium content analysis that utilize a vertical FD, the soil slurry may also be substantially free of surfactant and still achieve the desire optical clarity while the same optical clarity is not achieved in the absence of such surfactants in the horizontal FD.

According to the embodiments directed to the calcium analysis, non-limiting examples of reagents include potassium hydrogen phthalate, chlorophosphonazo III, and combinations thereof.

The reagents may comprise a first reagent that includes potassium hydrogen phthalate at a concentration of about 0.05 M to about 0.15 M—including all concentrations and sub-ranges there-between. The reagents may comprise a second reagent that includes chlorophosphonazo III in a concentration of about 0.5 ng to about 1.5 mg per mL of water—including all concentrations and sub-ranges there-between.

The calcium analysis may further comprise the addition of an extractant, which may be blended with the soil slurry. Non-limiting examples of extractant include ammonium acetate. The extractant may comprise ammonium acetate in concentration ranging from about 0.5 M to about 1.5 M—including all concentrations and sub-ranges there-between.

According to this embodiment, the soil sample may be prepared by mixing the filtrate with the first reagent, subsequently mixing with the second reagent, and subsequently performing the absorbance reading.

According to this embodiment, the soil slurry and soil mixture may not be subjected to a centrifuge force before performing the calcium absorbance reading.

Phosphorus Analysis

According to an embodiment of the present disclosure, phosphorus analysis may be performed according to the following methodology. A soil sample may be obtained and blended with liquid to create the soil slurry. The soil slurry may then flow through the filter element to create a filtrate, whereby one or more reagent may be added to the filtrate to create a mixture.

The soil mixture may then be analyzed for phosphorus content by absorbance that may be read via a spectrophotometer a wavelength ranging from 380 nm to 550 nm—preferably 410 nm to about 510 nm—including all sub-ranges and wavelengths there-between.

In some embodiments, the phosphorus content analysis may occur inside of the analysis tool 110 and as the soil mixture flows along the vertical FD, whereby the vertical FD is substantially parallel to gravitational direction GD such that the soil mixture flows downward at least partially under the effects of gravity. In some embodiments, the phosphorus content analysis may occur inside of the analysis tool 110a and as the soil mixture flows along the vertical FD, whereby the vertical FD is substantially parallel to gravitational direction GD such that the soil mixture flows upward against the effects of gravity.

In alternative embodiments, the phosphorus content analysis may occur inside of the analysis tool 210 and as the soil mixture flows along the horizontal FD, whereby the horizontal FD is substantially orthogonal to the gravitational direction GD and the soil slurry flows horizontally through the analysis tool 210.

According to embodiments of the phosphorus content analysis that utilize the vertical FD and horizontal FD, a surfactant may be added to the soil slurry. It has been surprisingly discovered that the addition of a non-ionic surfactant provides an unexpected improvement in optical clarity that enhances the spectrophotometer phosphorus content analysis while ionic surfactants fail to provide such improved optical properties. Non-limiting examples of non-ionic surfactant include 4-nonylphenyl polyethylene glycol, poly(ethylene glycol)(18) tridecylether, and mixtures thereof.

The surfactant of this embodiment may be substantially free of ionic compounds. The surfactant of this embodiment may be substantially free of cationic compounds. The surfactant of this embodiment may be substantially free of anionic compounds.

It has also been surprisingly discovered that for the embodiments of the phosphorus content analysis that utilize a vertical FD, the soil slurry may also be substantially free of surfactant and still achieve the desire optical clarity while the same optical clarity is not achieved in the absence of such surfactants in the horizontal FD.

According to the embodiments directed to the phosphorous analysis, non-limiting examples of reagents include ammonium molybdate in sulfuric acid.

According to the embodiments directed toward a horizontal FD used in phosphorus analysis, the reagents may comprise a first reagent that includes ammonium molybdate at a concentration of about 2.5% in sulfuric acid.

According to the embodiments directed toward a vertical FD used in phosphorus analysis, the reagents may comprise a first reagent that includes ammonium molybdate at a concentration of about 2.5% in sulfuric acid.

According to the embodiments directed toward a vertical FD used in phosphorus analysis, an extractant may be blended with the soil slurry. Non-limiting examples of extractant include HCl in ammonium fluoride or acetic acid in ammonium fluoride.

The extractant in the embodiments directed to the vertical FD may comprise HCl at a concentration of about 0.025 M in ammonium fluoride at a concentration of about 0.03 M. Alternatively, the extractant in the embodiments directed to the vertical FD may comprise acetic acid at a concentration of about 0.25 M in aqueous ammonium fluoride, the ammonium fluoride at a concentration of about 0.015 M.

The extractant in the embodiments directed to the horizontal FD may comprise HCl at a concentration of about 0.025 M in ammonium fluoride at a concentration of about 0.03 M. Alternatively, the extractant in the embodiments directed to the horizontal FD may comprise acetic acid at a concentration of about 0.25 M in aqueous ammonium fluoride, the ammonium fluoride at a concentration of about 0.015 M.

According to this embodiment, the soil sample may be prepared by mixing the filtrate with the first reagent and subsequently performing the absorbance reading.

According to this embodiment, the soil slurry and soil mixture may not be subjected to a centrifuge force before performing the phosphorus absorbance reading.

pH Test Analysis

According to an embodiment of the present disclosure, pH may be tested according to the following methodology. A soil sample may be obtained and blended with liquid to create the soil slurry. The soil slurry may then flow through the filter element to create a filtrate, whereby one or more indicators may be added to the filtrate to create a mixture.

The soil mixture may then be analyzed for pH by absorbance that may be read via a spectrophotometer at a wavelength of 575 nm or 615 nm.

In some embodiments, the pH test analysis may occur inside of the analysis tool 110 and as the soil mixture flows along the vertical FD, whereby the vertical FD is substantially parallel to gravitational direction GD such that the soil mixture flows downward at least partially under the effects of gravity. In some embodiments, the pH test analysis may occur inside of the analysis tool 110a and as the soil mixture flows along the vertical FD, whereby the vertical FD is substantially parallel to gravitational direction GD such that the soil mixture flows upward against the effects of gravity.

In alternative embodiments, the pH test analysis may occur inside of the analysis tool 210 and as the soil mixture flows along the horizontal FD, whereby the horizontal FD is substantially orthogonal to the gravitational direction GD and the soil slurry flows horizontally through the analysis tool 210.

According to embodiments of the pH test analysis that utilize vertical FD and horizontal FD, the soil slurry may comprise a surfactant. It has been surprisingly discovered that the addition of a non-ionic surfactant provides an unexpected improvement in optical clarity that enhances the spectrophotometer pH test analysis while ionic surfactants fail to provide such improved optical properties. Non-limiting examples of non-ionic surfactant include 4-nonylphenyl polyethylene glycol, poly(ethylene glycol)(18) tridecylether, and mixtures thereof. The surfactant of this embodiment may be substantially free of ionic surfactant. The surfactant of this embodiment may be substantially free of anionic surfactant. The surfactant of this embodiment may be substantially free of cationic surfactant.

It has also been surprisingly discovered that for the embodiments of the pH test analysis that utilize a vertical FD, the soil slurry may also be substantially free of surfactant and still achieve the desire optical clarity while the same optical clarity is not achieved in the absence of such surfactants in the horizontal FD.

According to the embodiments directed to the pH analysis, non-limiting examples of indicator may include chlorophenol red sodium salt, phenol red sodium salt, Bromocresol Green sodium salt, Bromocresol green (2,6-Dibromo-4-[7-(3,5-dibromo-4-hydroxy-2-methyl-phenyl)-9,9-dioxo-8-oxa-9k6-thiabicyclo[4.3.0]nona-1,3,5-trien-7-yl]-3-methyl-phenol, 3,3',5,5'-Tetrabromo-m-cresolsulfonphthalein Bromocresol green, CAS 76-60-8) with Nitrazine yellow (2-(2,4-Dinitrophenylazo)-1-hydroxynaphthalene-3,6-disulfonic acid disodium salt, 2-(2,4-Dinitrophenylazo)naphthol-3,6-disulfonic acid disodium salt, Nitrazol Yellow, CAS 5423-07-4).

In one embodiment, the indicator composition may include Bromocresol green and Nitrazine yellow in a weight ratio of Bromocresol green to Nitrazine yellow of 0.1:1 to 100:1. In other embodiments, the weight ratio is 0.2:1 to 20:1. In one embodiment, the indicator composition may include 0.01 wt. % to 0.02 wt. % Bromocresol green, 0.0125 wt. % to 0.025 wt. % Nitrazine yellow, and a liquid.

In one embodiment, the indicator may include 0.01 wt. % to about 0.08 wt. % of Bromocresol green sodium salt and 0.01 wt. % to about 0.1 wt. % of Nitrazine yellow. In one embodiment, the indicator may include 0.02 wt. % of Bromocresol Green sodium salt and 0.025 wt. % of Nitrazine yellow. In one embodiment, the indicator may include Bromocresol Green sodium salt and Nitrazine yellow in a 1:1 weight ratio.

In one embodiment, the indicator may include 0.01 wt. % to about 0.08 wt. % of chlorophenol red sodium salt and 0.01 wt, % to about 0.1 wt, % of phenol red sodium salt. In one embodiment, the indicator may include 0.04 wt. % of chlorophenol red sodium salt and 0.05 wt. % of phenol red sodium salt. In one embodiment, the indicator may include chlorophenol red sodium salt and phenol red sodium salt in a 1:1 weight ratio.

Optionally, a flocculating agent can be added (as described above, for example using polyacrylamide as described above). The flocculating agent amount may be chosen to remove organic materials and/or reduce or eliminate cloudiness. In one embodiment, a 0.017M $CaCl_2 \cdot 2H_2O$ solution is used. Alternatively, the anhydride or other hydrates of calcium chloride may be used. In one embodiment, a molar concentration for calcium chloride is 0.005M to 0.1M—including all concentrations and sub-ranges there-between.

The soil slurry may be mixed with the flocculating agent in a volume ratio of 9:1 soil slurry:flocculating agent. In other embodiments, a volume ratio of slurry to flocculating agent may be 1:1 to 10:1—including all ratios and sub-ranges there-between. In another embodiment, the calcium chloride solution can be replaced with a 0.025 weight % polyacrylamide solution. In one embodiment, the polyacrylamide can have a weight average molecular weight of 5,000,000 to 6,000,000 (CAS 9003-05-8). Other flocculating agents can be used in amounts that provide the same amount of flocculation as the above calcium chloride or polyacrylamide solutions. The soil slurry and flocculating agent are centrifuged to form the soil extract.

In a non-limiting example of the liquid is water, but other liquids can be used.

According to the embodiments directed toward a vertical FD used in pH analysis, an extractant may be blended with the soil slurry. Non-limiting examples of extractant include calcium chloride, potassium chloride, sodium chloride, or magnesium chloride. The extractant may be present in concentration ranging from about 0.05 M to about 0.15 M—including all concentrations and sub-ranges there-between. In one embodiment, the extractant comprises calcium chloride in a concentration of about 0.1 M.

In some embodiments, the soil sample may be prepared by mixing the filtrate with the indicator and subsequently performing the absorbance reading at 615 nm when using indicator that includes Bromocresol Green sodium salt and Nitrazine yellow.

In some embodiments, the soil sample may be prepared by mixing the filtrate with the indicator and subsequently performing the absorbance reading at 575 nm when using indicator that includes chlorophenol red sodium salt and phenol red sodium salt.

According to this embodiment, the soil slurry and soil mixture may not be subjected to a centrifuge force before performing the pH absorbance reading.

Buffer pH Test Analysis

According to an embodiment of the present disclosure, buffer pH may be tested according to the following methodology. A soil sample may be obtained and blended with liquid to create the soil slurry. The soil slurry may then flow through the filter element to create a filtrate, whereby one or more indicators may be added to the filtrate to create a mixture.

The soil mixture may then be analyzed for buffer pH by absorbance that may be read via a spectrophotometer at a wavelength of about 575 nm.

The buffer pH analysis may occur inside of the analysis tool 110 and as the soil mixture flows along the vertical FD, whereby the vertical FD is substantially parallel to gravitational direction GD such that the soil mixture flows downward at least partially under the effects of gravity. In some embodiments, the buffer pH analysis may occur inside of the analysis tool 110a and as the soil mixture flows along the vertical FD, whereby the vertical FD is substantially parallel to gravitational direction GD such that the soil mixture flows upward against the effects of gravity.

In alternative embodiments, the buffer pH analysis may occur inside of the analysis tool 210 and as the soil mixture flows along the horizontal FD, whereby the horizontal FD is substantially orthogonal to the gravitational direction GD and the soil slurry flows horizontally through the analysis tool 210.

According to embodiments of the pH buffer analysis that utilize a vertical FD and horizontal FD, the soil slurry may comprise a surfactant. It has been surprisingly discovered that the addition of a non-ionic surfactant provides an unexpected improvement in optical clarity that enhances the spectrophotometer pH buffer analysis while ionic surfactants fail to provide such improved optical properties. Non-limiting examples of non-ionic surfactant include 4-non-ylphenyl polyethylene glycol, poly(ethylene glycol)(18) tridecylether, and mixtures thereof. The surfactant of this embodiment may be substantially free of ionic surfactant. The surfactant of this embodiment may be substantially free of anionic surfactant. The surfactant of this embodiment may be substantially free of cationic surfactant.

It has also been surprisingly discovered that for the embodiments of the pH buffer analysis that utilize a vertical FD, the soil slurry may also be substantially free of surfactant and still achieve the desire optical clarity while the same optical clarity is not achieved in the absence of such surfactants in the horizontal FD.

According to the embodiments directed to the pH analysis, non-limiting examples of indicator may include chlorophenol red sodium salt, phenol red sodium salt, methyl red (2-{[4-(Dimethylamino)phenyl]diazenyl}benzoic acid) with bromothymol blue (4,4'-(1,1-Dioxido-3H-2,1-benzoxathiole-3,3-diyl)bis(2-bromo-6-isopropyl-3-methylphenol), CAS 76-59-5).

In one embodiment, there is a composition that includes methyl red and bromothymol blue in a molar ratio of 2.5:1 to 50:1. In other embodiments, the molar ratio is 20:1 to 30:1 or about 25:1. The mixed indicator solution is made by taking 1% methyl red indicator in water and mixing it 1:1 with 0.04% bromothymol blue in a 90/10 water/ethanol mixture to make a final concentration of 0.5% methyl red, 0.02% bromothymol blue in a 95/5 water/ethanol solution by weight.

In one embodiment, the indicator may include 0.01 wt. % to about 0.08 wt. % of chlorophenol red sodium salt and 0.01 wt. % to about 0.1 wt. % of phenol red sodium salt. In one embodiment, the indicator may include 0.02 wt. % of chlorophenol red sodium salt and 0.025 wt. % of phenol red sodium salt in water. In one embodiment, the indicator may include chlorophenol red sodium salt and phenol red sodium salt in a 1:1 weight ratio.

According to the embodiments directed toward a vertical FD used in pH analysis, an extractant may be blended with the soil slurry.

In another embodiment, the buffer pH of a soil extract can be measured by obtaining a soil extract, combining with a buffer, adding methyl red and bromothymol blue to the soil extract to form a mixture, and then measuring absorbance of the mixture. In some embodiments, the buffer is added to the soil extract before adding the methyl red and bromothymol blue. The soil extract can be prepared as described above for the soil slurry. The soil slurry can be combined with a buffer solution in a volume ratio of 9:1 slurry to buffer. In one embodiment, the volume ratio is 1:1 to 11:1. In one embodiment, the buffer solution is Sikora buffer. Sikora buffer is available from GFS Chemicals of Powell, Ohio, and it is about 85.6% water, 13.7% potassium chloride, 0.278% triethanol amine and balance minors. Optionally, a flocculating agent can be added (as described above, for example using polyacrylamide as described above) and centrifuged to form a filtrate.

In a non-limiting example of the liquid is water, but other liquids can be used.

In some embodiments, the soil sample may be prepared by mixing the 2 mL of the filtrate with 0.2 mL of the indicator and subsequently performing the absorbance reading at 575 nm when using indicator that includes chlorophenol red sodium salt and phenol red sodium salt.

According to this embodiment, the soil slurry and soil mixture may not be subjected to a centrifuge force before performing the pH absorbance reading.

To perform the absorbance readings, a calibration curve can be obtained and used with the correlation chart. Soil slurry before adding indicator composition is measured for absorbance to establish a blank reading. The indicator composition (as described above) is then added to this sample and remeasured for absorbance. The difference in the absorbance readings is used for a calibration curve. This calibration can be done as needed, such as once per day. The calibration curve is used to adjust the correlation chart.

Cartridge

In one embodiment, a multi-chamber cartridge can be provided in which each chamber contains one of the above compositions in a combination that tests for at least two of the above listed tests (e.g., two or more of the pH test, buffer pH test, potassium test, phosphorous test, calcium test, and/or magnesium tests). In one embodiment, the cartridge has a chamber for the pH test composition, a chamber for the buffer pH test composition, a chamber for the potassium test composition, a chamber for the phosphorous test composition, a chamber for the calcium test composition, and a chamber for the magnesium test composition. In one embodiment, any of the cartridges can contain an additional chamber that does not contain any of the compositions for the above tests.

EXAMPLES

A number of experiments were performed to test the impact of flow configuration and surfactant during soil analysis. For the purposes of these experiments, the flow directions ("FD") were tested at a substantially horizontal orientation (herein referred to as "H"), whereby the angle of the horizontal FD was substantially orthogonal to the gravitational direction ("GD"), and the FD was tested at a substantially vertical orientation (herein referred to as "V"), whereby the angle of the vertical FD was substantially parallel to the GD.

Experiment 1—Potassium Analysis

A first experiment was performed to test the impact of horizontal FD and vertical FD as it relates to surfactant for a potassium soil analysis.

The samples of Examples 1-4 were prepared by blending soil and water together at a 1:3 ratio to create a slurry, whereby the slurry is pulled into the extraction portion of the system and potassium is extracted in a 1:3 ratio of slurry to extractant with 0.03 M nitric acid. After extraction, the extracted samples were filtered and the filtrate was subsequently blended with reagent to create a soil mixture, the reagent including lithium hydroxide solution and then subsequently mixed with tetraphenylborate in NaOH, and subsequently, each sample is mixed with sodium tetraborate decahydrate in glycerol and sodium dodecyl sulfate (SDS) in an aqueous solution. Each soil mixture of Examples 1-4 was then flowed along the horizontal FD through the analysis tool.

The sample of Example 1 included a non-ionic surfactant. The sample of Example 2 included an anionic surfactant.

The sample of Example 3 included a cationic surfactant. The sample of Example 4 was free of surfactant.

The samples of Examples 5-8 were prepared by blending soil and water together at a 1:3 ratio to create a slurry, whereby the slurry is pulled into the extraction portion of the system and potassium is extracted in a 1:3 ratio of slurry to extractant with 0.03 M nitric acid. After extraction, the extracted samples were filtered and the filtrate was subsequently blended with reagent to create a soil mixture, the reagent including lithium hydroxide solution and then subsequently mixed with tetraphenylborate in NaOH, and subsequently, each sample is mixed with sodium tetraborate decahydrate in glycerol and sodium dodecyl sulfate (SDS) in an aqueous solution. Each soil mixture of Examples 1-4 was then flowed along the vertical FD through the analysis tool.

The sample of Example 5 included a non-ionic surfactant. The sample of Example 6 included an anionic surfactant. The sample of Example 7 included a cationic surfactant. The sample of Example 8 was free of surfactant.

Each sample of Examples 1-8 was analyzed by the analysis tool at a wavelength between 380-550 nm to determine the potassium concentration in the sample. After mixing, each sample produces turbidity and the ability to read through each sample was recorded as either a pass or fail value—whereby the pass value equates to an optical property sufficiently clear to allow for the reading of the potassium concentration at a wavelength between 380-550 nm and the fail value equates to an optical property insufficiently clear to not allow for reading of the potassium concentration at a wavelength between 380-550 nm. The results are set forth below in Table 1.

TABLE 1

|  | Ex. 1 | Ex. 2 | Ex. 3 | Ex. 4 | Ex. 5 | Ex. 6 | Ex. 7 | Ex. 8 |
|---|---|---|---|---|---|---|---|---|
| FD | H | H | H | H | V | V | V | V |
| Non-Ionic Surfactant | Y | N | N | N | Y | N | N | N |
| Anionic Surfactant | N | Y | N | N | N | Y | N | N |
| Cationic Surfactant | N | N | Y | N | N | N | Y | N |
| No Surfactant | N | N | N | Y | N | N | N | Y |
| Optical Analysis | Fail | Pass | Fail | Fail | Fail | Pass | Fail | Pass | clarity for the potassium analysis as compared to the horizontal FD filtration systems which surprisingly failed the same test.

Experiment 2—Magnesium Analysis

A second experiment was performed to test the impact of horizontal FD and vertical FD as it relates to surfactant for a magnesium soil analysis.

The samples of Examples 9-12 were prepared by blending soil and water together at a 1:3 ratio to create a slurry, whereby the slurry is pulled into the extraction portion of the system and magnesium is extracted in a 1:3 ratio of slurry to extractant with ammonium acetate. After extraction, the extracted samples were filtered and the filtrate was subsequently blended with reagent to create a soil mixture, the reagent including Tetrabutylammonium hydroxide and boric acid and subsequently mixed with Chlorophosphonazo III. Each soil mixture of Examples 9-12 was then flowed along the horizontal FD through the analysis tool.

The sample of Example 9 included a non-ionic surfactant. The sample of Example 10 included an anionic surfactant. The sample of Example 11 included a cationic surfactant. The sample of Example 12 was free of surfactant.

The samples of Examples 13-16 were prepared by blending soil and water together at a 1:3 ratio to create a slurry, whereby the slurry is pulled into the extraction portion of the system and magnesium is extracted in a 1:3 ratio of slurry to extractant with ammonium acetate. After extraction, the extracted samples were filtered and the filtrate was subsequently blended with reagent to create a soil mixture, the reagent including Tetrabutylammonium hydroxide and boric acid and subsequently mixed with Chlorophosphonazo III. Each soil mixture of Examples 13-16 were then flowed along the vertical FD through the analysis tool.

The sample of Example 13 included a non-ionic surfactant. The sample of Example 14 included an anionic surfactant. The sample of Example 15 included a cationic surfactant. The sample of Example 16 was free of surfactant.

Each sample of Examples 9-16 was analyzed by the analysis tool at a wavelength between 600-690 nm to determine the magnesium concentration in the sample. After mixing, each sample produces turbidity, and the ability to read through each sample was recorded as either a pass or fail—whereby the pass value equates to an optical property sufficiently clear to allow for the reading of the magnesium concentration at a wavelength between 600-690 nm and the fail value equates to an optical property insufficiently clear to not allow for reading of the magnesium concentration at a wavelength between 600-690 nm. The results are set forth below in Table 2.

TABLE 2

|  | Ex. 9 | Ex. 10 | Ex. 11 | Ex. 12 | Ex. 13 | Ex. 14 | Ex. 15 | Ex. 16 |
|---|---|---|---|---|---|---|---|---|
| FD | H | H | H | H | V | V | V | V |
| Non-Ionic Surfactant | Y | N | N | N | Y | N | N | N |
| Anionic Surfactant | N | Y | N | N | N | Y | N | N |
| Cationic Surfactant | N | N | Y | N | N | N | Y | N |
| No Surfactant | N | N | N | Y | N | N | N | Y |
| Optical Analysis | Pass | Fail | Fail | Fail | Pass | Fail | Fail | Pass |

As demonstrated by Table 1, it was discovered that the addition of anionic surfactant provided for the optical clarity needed to perform the potassium analysis at wavelengths of 380 nm to 550 nm when operating in the horizontal FD and vertical FD while non-anionic surfactants failed such test. Table 1 also demonstrates that no surfactant in the filtration systems having a vertical FD exhibited sufficient optical As demonstrated by Table 2, it was discovered that the addition of non-ionic surfactant provided for the optical clarity needed to perform the magnesium analysis at wavelengths of 600 nm to 690 nm when operating in the horizontal FD and vertical FD while ionic surfactants failed such test. Table 2 also demonstrates that no surfactant in the filtration systems having a vertical FD exhibited sufficient optical clarity for the magnesium analysis as compared to the horizontal FD filtration systems which surprisingly failed the same test.

Experiment 3—Calcium Analysis

A third experiment was performed to test the impact of horizontal FD and vertical FD as it relates to surfactant for a calcium soil analysis.

The samples of Examples 17-20 were prepared by blending soil and water together at a 1:3 ratio to create a slurry, whereby the slurry is pulled into the extraction portion of the system and potassium is extracted in a 1:3 ratio of slurry to extractant with ammonium acetate. After extraction, the extracted samples were filtered and the filtrate was subsequently blended with reagent to create a soil mixture, the reagent including potassium hydrogen phthalate and subsequently Chlorophosphonazo III. Each soil mixture of Examples 17-20 was then flowed along the horizontal FD through the analysis tool.

The sample of Example 17 included a non-ionic surfactant. The sample of Example 18 included an anionic surfactant. The sample of Example 19 included a cationic surfactant. The sample of Example 20 was free of surfactant.

The samples of Examples 21-24 were prepared by blending soil and water together at a 1:3 ratio to create a slurry, whereby the slurry is pulled into the extraction portion of the system and potassium is extracted in a 1:3 ratio of slurry to extractant with ammonium acetate. After extraction, the extracted samples were filtered and the filtrate was subsequently blended with reagent to create a soil mixture, the reagent including potassium hydrogen phthalate and subsequently Chlorophosphonazo III. Each soil mixture of Examples 21-24 was then flowed along the vertical FD through the analysis tool.

The sample of Example 21 included a non-ionic surfactant. The sample of Example 22 included an anionic surfactant. The sample of Example 23 included a cationic surfactant. The sample of Example 24 was free of surfactant.

Each sample of Examples 17-24 was analyzed by the analysis tool at a wavelength of 615 nm to determine the calcium concentration in the sample. After mixing, each sample produces turbidity, and the ability to read through each sample was recorded as either a pass or fail—whereby the pass value equates to an optical property sufficiently clear to allow for the reading of the calcium concentration at a wavelength of 615 nm and the fail value equates to an optical property insufficiently clear to not allow for reading of the calcium concentration at a wavelength of 615 nm. The results are set forth below in Table 3.

As demonstrated by Table 3, it was discovered that the addition of non-ionic surfactant provided for the optical clarity needed to perform the magnesium analysis at a wavelength of 615 nm when operating in the horizontal FD and vertical FD while ionic surfactants failed such test. Table 3 also demonstrates that no surfactant in the filtration systems having a vertical FD exhibited sufficient optical clarity for the calcium analysis as compared to the horizontal FD filtration systems which surprisingly failed the same test.

Experiment 4—Phosphorus Analysis

A fourth experiment was performed to test the impact of horizontal FD and vertical FD as it relates to surfactant for a phosphorus soil analysis.

The samples of Examples 25-32 were prepared by blending soil and water together at a 1:3 ratio to create a slurry, whereby the slurry is pulled into the extraction portion of the system and potassium is extracted in a 1:3 ratio of slurry to extractant, the extractant selected from either HCl in ammonium fluoride or acetic acid in ammonium fluoride. After extraction, each extracted sample is filtered, and the filtrate of each sample was then mixed with ammonium molybdate in sulfuric acid.

Each soil mixture of Examples 25-28 was then flowed along the horizontal FD through the analysis tool, and each soil mixture of Examples 29-32 was then flowed along the vertical FD through the analysis tool.

The sample of Example 25 included a non-ionic surfactant. The sample of Example 26 included an anionic surfactant. The sample of Example 27 included a cationic surfactant. The sample of Example 28 was free of surfactant. The sample of Example 29 included a non-ionic surfactant. The sample of Example 30 included an anionic surfactant. The sample of Example 31 included a cationic surfactant. The sample of Example 32 was free of surfactant.

Each sample of Examples 25-32 were analyzed by the analysis tool at a wavelength between 380-550 nm to determine the phosphorus concentration in the sample. After mixing, each sample produces turbidity, and the ability to read through each sample was recorded as either a pass or fail—whereby the pass value equates to an optical property sufficiently clear to allow for the reading of the phosphorus concentration at a wavelength between 380-550 nm and the fail value equates to an optical property insufficiently clear to not allow for reading of the phosphorus concentration at a wavelength between 380-550 nm. The results are set forth below in Table 4.

TABLE 3

|  | Ex. 17 | Ex. 18 | Ex. 19 | Ex. 20 | Ex. 21 | Ex. 22 | Ex. 23 | Ex. 24 |
|---|---|---|---|---|---|---|---|---|
| FD | H | H | H | H | V | V | V | V |
| Non-Ionic Surfactant | Y | N | N | N | Y | N | N | N |
| Anionic Surfactant | N | Y | N | N | N | Y | N | N |
| Cationic Surfactant | N | N | Y | N | N | N | Y | N |
| No Surfactant | N | N | N | Y | N | N | N | Y |
| Optical Analysis | Pass | Fail | Fail | Fail | Pass | Fail | Fail | Pass |

TABLE 4

| | Ex. 25 | Ex. 26 | Ex. 27 | Ex. 28 | Ex. 29 | Ex. 30 | Ex. 31 | Ex. 32 |
|---|---|---|---|---|---|---|---|---|
| FD | H | H | H | H | V | V | V | V |
| Non-Ionic Surfactant | Y | N | N | N | Y | N | N | N |
| Anionic Surfactant | N | Y | N | N | N | Y | N | N |
| Cationic Surfactant | N | N | Y | N | N | N | Y | N |
| No Surfactant | N | N | N | Y | N | N | N | Y |
| Optical Analysis | Pass | Fail | Fail | Fail | Pass | Fail | Fail | Pass |

As demonstrated by Table 4, it was discovered that the addition of non-ionic surfactant provided for the optical clarity needed to perform the phosphorus analysis at wavelengths of 380 nm to 550 nm when operating in the horizontal FD and vertical FD while ionic surfactants failed such test. Table 4 also demonstrates that no surfactant in the filtration systems having a vertical FD exhibited sufficient optical clarity for the phosphorus analysis as compared to the horizontal FD filtration systems which surprisingly failed the same test.

Experiment 5—pH Analysis

A fifth experiment was performed to test the impact of horizontal FD and vertical FD as it relates to surfactant for a pH soil analysis.

The samples of Examples 33-40 were prepared by blending soil and water together at a 1:3 ratio to create a slurry, whereby the slurry is pulled into the extraction portion of the system and extractant is added at a 1:3 ratio of slurry to extractant, with the extractant being 0.1 M calcium chloride. After extraction, the extracted samples were filtered and the filtrate was subsequently blended with indicator to create a soil mixture, the indicator including a 1:1 ratio of bromocresol green sodium salt and nitrazine yellow. Each soil mixture of Examples 33-36 was then flowed along the horizontal FD through the analysis tool, and each soil mixture of Examples 37-40 was then flowed along the vertical FD through the analysis tool.

The sample of Example 33 included a non-ionic surfactant. The sample of Example 34 included an anionic surfactant. The sample of Example 35 included a cationic surfactant. The sample of Example 36 was free of surfactant. The sample of Example 37 included a non-ionic surfactant. The sample of Example 38 included an anionic surfactant. The sample of Example 39 included a cationic surfactant. The sample of Example 40 was free of surfactant.

Each sample of Examples 33-40 was analyzed by the analysis tool at a wavelength of 615 nm to determine the pH in the sample. After mixing, each sample produces turbidity and the ability to read through each sample was recorded as either a pass or fail value—whereby the pass value equates to an optical property sufficiently clear to allow for the reading of the pH a wavelength of 615 nm the fail value equates to an optical property insufficiently clear to not allow for reading of the pH at a wavelength of 615 nm. The results are set forth below in Table 5.

As demonstrated by Table 5, it was discovered that the addition of non-ionic surfactant provided for the optical clarity needed to perform the pH test analysis at a wavelength of 615 nm when operating in the horizontal FD and vertical FD while ionic surfactants failed such test. Table 5 also demonstrates that no surfactant in the filtration systems having a vertical FD exhibited sufficient optical clarity for the pH test analysis as compared to the horizontal FD filtration systems which surprisingly failed the same test.

Experiment 6—Buffer pH Analysis

A sixth experiment was performed to test the impact of horizontal FD and vertical FD as it relates to surfactant for a buffer pH soil analysis.

The samples of Examples 41-48 were prepared by blending soil and water together at a 1:3 ratio to create a slurry, whereby the slurry is pulled into the extraction portion of the system and extractant is added at a 1:3 ratio of slurry to extractant, with the extractant being Sikora buffer. After extraction, the extracted samples were filtered and the filtrate was subsequently blended with indicator to create a soil mixture, the indicator including a 1:1 ratio of chlorophenol red sodium salt and phenol red sodium salt. Each soil mixture of Examples 41-44 was then flowed along the horizontal FD through the analysis tool, and each soil mixture of Examples 45-48 was then flowed along the vertical FD through the analysis tool.

The sample of Example 41 included a non-ionic surfactant. The sample of Example 42 included an anionic surfactant. The sample of Example 43 included a cationic surfactant. The sample of Example 44 was free of surfactant. The sample of Example 45 included a non-ionic surfactant. The sample of Example 46 included an anionic surfactant. The sample of Example 47 included a cationic surfactant. The sample of Example 48 was free of surfactant.

Each sample of Examples 41-44 was analyzed by the analysis tool at a wavelength of 575 nm to determine the buffer pH in the sample. After mixing, each sample produces turbidity and the ability to read through each sample was recorded as either a pass or fail value—whereby the pass value equates to an optical property sufficiently clear to allow for the reading of the buffer pH a wavelength of 575 nm the fail value equates to an optical property insufficiently clear to not allow for reading of the buffer pH at a wavelength of 575 nm. The results are set forth below in Table 6.

TABLE 5

| | Ex. 33 | Ex. 34 | Ex. 35 | Ex. 36 | Ex. 37 | Ex. 38 | Ex. 39 | Ex. 40 |
|---|---|---|---|---|---|---|---|---|
| FD | H | H | H | H | V | V | V | V |
| Non-Ionic Surfactant | Y | N | N | N | Y | N | N | N |
| Anionic Surfactant | N | Y | N | N | N | Y | N | N |
| Cationic Surfactant | N | N | Y | N | N | N | Y | N |
| No Surfactant | N | N | N | Y | N | N | N | Y |
| Optical Analysis | Pass | Fail | Fail | Fail | Pass | Fail | Fail | Pass |

TABLE 6

|                    | Ex. 41 | Ex. 42 | Ex. 43 | Ex. 44 | Ex. 45 | Ex. 46 | Ex. 47 | Ex. 48 |
|--------------------|--------|--------|--------|--------|--------|--------|--------|--------|
| FD                 | H      | H      | H      | H      | V      | V      | V      | V      |
| Non-Ionic Surfactant | Y    | N      | N      | N      | Y      | N      | N      | N      |
| Anionic Surfactant | N      | Y      | N      | N      | N      | Y      | N      | N      |
| Cationic Surfactant | N     | N      | Y      | N      | N      | N      | Y      | N      |
| No Surfactant      | N      | N      | N      | Y      | N      | N      | N      | Y      |
| Optical Analysis   | Pass   | Fail   | Fail   | Fail   | Pass   | Fail   | Fail   | Pass   |

As demonstrated by Table 6, it was discovered that the addition of non-ionic surfactant provided for the optical clarity needed to perform the pH buffer analysis at a wavelength of 575 nm when operating in the horizontal FD and vertical FD while ionic surfactants failed such test. Table 6 also demonstrates that no surfactant in the filtration systems having a vertical FD exhibited sufficient optical clarity for the pH buffer analysis as compared to the horizontal FD filtration systems which surprisingly failed the same test.

EMBODIMENTS

The following are non-limiting embodiments.

Embodiment 1. A method of analyzing potassium content in soil, the method comprising: a) obtaining a soil sample; b) adding a liquid to the soil sample to form a soil slurry; c) flowing the soil slurry through a filter to form a filtrate; d) blending a reagent composition with the filtrate to form a soil mixture; and e) flowing the soil mixture through an analysis tool along a flow direction whereby a potassium absorbance of the soil mixture is measured; and wherein the flow direction is oriented such that the soil mixture flows vertically.

Embodiment 2. The method according to embodiment 1, wherein the liquid comprises water and the soil slurry of step b) is formed at a weight ratio of soil sample to liquid ranging from about 1:2 to about 1:4.

Embodiment 3. The method according to any one of embodiments 1 to 2, wherein the reagent composition includes a first reagent comprising lithium hydroxide and a second reagent comprising tetraphenylborate in sodium hydroxide, and wherein the reagent composition includes a third reagent comprising sodium tetraborate decahydrate in aqueous glycerol.

Embodiment 4. The method according to any one of embodiments 1 to 3, wherein an extractant is blended with the soil slurry, the extractant comprises nitric acid.

Embodiment 5. The method according to any one of embodiments 1 to 4, wherein the soil slurry of steps b) and c) and the soil mixture of step e) are substantially free of surfactant.

Embodiment 6. The method according to any one of embodiments 1 to 4, wherein the soil slurry of steps b) and c) and the soil mixture of step e) comprise an anionic surfactant.

Embodiment 7. The method according to embodiment 6, wherein the anionic surfactant is selected from sodium laurate phosphate, sodium laurate sulfate, and sodium dodecyl sulfate.

Embodiment 8. The method according to any one of embodiments 6 to 7, wherein the soil slurry of steps b) and c) and the soil mixture of step e) is substantially free of cationic surfactant.

Embodiment 9. A method of analyzing magnesium content in soil, the method comprising: a) obtaining a soil sample; b) adding a liquid to the soil sample to form a soil slurry; c) flowing the soil slurry through a filter to form a filtrate; d) blending a reagent composition with the filtrate to form a soil mixture; and e) flowing the soil mixture through an analysis tool along a flow direction whereby a magnesium absorbance of the soil mixture is measured; and wherein the flow direction is oriented such that the soil mixture flows vertically.

Embodiment 10. The method according to embodiment 9, wherein the liquid comprises water and the soil slurry of step b) is formed at a weight ratio of soil sample to liquid ranging from about 1:2 to about 1:4.

Embodiment 11. The method according to any one of embodiments 9 to 10, wherein the reagent composition includes a first reagent comprising tetrabutylammonium hydroxide and boric acid and a second reagent comprising chlorophosphonazo III.

Embodiment 12. The method according to any one of embodiments 9 to 12, wherein an extractant is blended with the soil slurry, wherein the extractant comprises ammonium acetate.

Embodiment 13. The method according to any one of embodiments 9 to 13, wherein the soil slurry of steps b) and c) and the soil mixture of step e) are substantially free of surfactant.

Embodiment 14. The method according to any one of embodiments 9 to 13, wherein the soil slurry of steps b) and c) and the soil mixture of step e) comprise a non-ionic surfactant.

Embodiment 15. The method according to embodiment 14, wherein the non-ionic surfactant is selected from 4-nonylphenyl polyethylene glycol and poly(ethylene glycol)(18) tridecylether.

Embodiment 16. The method according to any one of embodiments 14 to 15, wherein the soil slurry of steps b) and c) and the soil mixture of step e) are substantially free of ionic surfactant.

Embodiment 17. A method of analyzing calcium content in soil, the method comprising: a) obtaining a soil sample; b) adding a liquid to the soil sample to form a soil slurry; c) flowing the soil slurry through a filter to form a filtrate; d) blending a reagent composition with the filtrate to form a soil mixture; and e) flowing the soil mixture through an analysis tool along a flow direction whereby a calcium absorbance of the soil mixture is measured; and wherein the flow direction is oriented such that the soil mixture flows vertically.

Embodiment 18. The method according to embodiment 17, wherein the liquid comprises water and the soil slurry of step b) is formed at a weight ratio of soil sample to liquid ranging from about 1:2 to about 1:4.

Embodiment 19. The method according to anyone of embodiments 17 to 18, wherein the reagent composition includes a first reagent comprising potassium hydrogen phthalate and a second reagent comprising chlorophosphonazo III.

Embodiment 20. The method according to any one of embodiments 17 to 20, wherein an extractant is blended with the soil slurry, wherein the extractant comprises ammonium acetate.

Embodiment 21. The method according to any one of embodiments 17 to 20, the soil slurry of steps b) and c) and the soil mixture of step e) are substantially free of surfactant.

Embodiment 22. The method according to any one of embodiments 17 to 21, the soil slurry of steps b) and c) and the soil mixture of step e) comprises a non-ionic surfactant.

Embodiment 23. The method according to embodiment 22, wherein the non-ionic surfactant is selected from 4-non-ylphenyl polyethylene glycol and poly(ethylene glycol)(18) tridecylether.

Embodiment 24. The method according to any one of embodiments 22 to 23, the soil slurry of steps b) and c) and the soil mixture of step e) are substantially free of ionic surfactant.

Embodiment 25. A method of analyzing phosphorus content in soil, the method comprising: a) obtaining a soil sample; b) adding a liquid to the soil sample to form a soil slurry; c) flowing the soil slurry through a filter to form a filtrate; d) blending a reagent composition with the filtrate to form a soil mixture; and e) flowing the soil mixture through an analysis tool along a flow direction whereby a phosphorus absorbance of the soil mixture is measured; wherein the flow direction is oriented such that the soil mixture flows vertically.

Embodiment 26. The method according to embodiment 25, wherein the liquid comprises water and the soil slurry of step b) is formed at a weight ratio of soil sample to liquid ranging from about 1:2 to about 1:4.

Embodiment 27. The method according to any one of embodiments 25 to 26, wherein the reagent composition includes a first reagent comprising ammonium molybdate and sulfuric acid.

Embodiment 28. The method according to any one of embodiments 25 to 27, wherein an extractant is blended with the soil slurry, wherein the extractant is selected from a first blend of HCl and ammonium fluoride and a second blend of acetic acid and aqueous ammonium fluoride.

Embodiment 29. The method according to any one of embodiments 25 to 28, the soil slurry of steps b) and c) and the soil mixture of step e) are substantially free of surfactant.

Embodiment 30. The method according to any one of embodiments 25 to 28, the soil slurry of steps b) and c) and the soil mixture of step e) comprises a non-ionic surfactant.

Embodiment 31. The method according to embodiment 30, wherein the non-ionic surfactant is selected from 4-non-ylphenyl polyethylene glycol and poly(ethylene glycol)(18) tridecylether.

Embodiment 32. The method according to any one of embodiments 30 to 31, the soil slurry of steps b) and c) and the soil mixture of step e) are substantially free of ionic surfactant.

Embodiment 33. A method of analyzing potassium content in soil, the method comprising: a) obtaining a soil sample; b) adding a liquid to the soil sample to form a soil slurry; c) flowing the soil slurry through a filter to form a filtrate; d) blending a reagent composition with the filtrate to form a soil mixture; and e) flowing the soil mixture through an analysis tool along a flow direction whereby a potassium absorbance of the soil mixture is measured; and wherein the soil mixture comprises a surfactant and the flow direction is substantially horizontal and orthogonal to the direction of gravity.

Embodiment 34. The method according to embodiment 33, wherein the liquid comprises water and the soil slurry of step b) is formed at a weight ratio of soil sample to liquid ranging from about 1:1 to about 1:5.

Embodiment 35. The method according to any one of embodiments 33 to 34, wherein the reagent composition includes a first reagent comprising lithium hydroxide is present.

Embodiment 36. The method according to embodiment 35, wherein the reagent composition includes a second reagent comprising tetraphenylborate and sodium hydroxide and a third reagent comprising sodium tetraborate decahydrate and aqueous glycerol.

Embodiment 37. The method according to any one of embodiments 33 to 36, wherein an extractant is blended with the soil slurry, wherein the extractant is nitric acid.

Embodiment 38. The method according to any one of embodiments 33 to 37, wherein the surfactant is an anionic surfactant.

Embodiment 39. The method according to embodiment 38, wherein the anionic surfactant is selected from sodium laurate phosphate, sodium laurate sulfate, and sodium dodecyl sulfate.

Embodiment 40. The method according to any one of embodiments 33 to 39, wherein the surfactant is substantially free of cationic compounds.

Embodiment 41. The method according to any one of embodiments 33 to 40, wherein the surfactant is substantially free of non-ionic compounds.

Embodiment 42. A method of analyzing magnesium content in soil, the method comprising: a) obtaining a soil sample; b) adding a liquid to the soil sample to form a soil slurry; c) flowing the soil slurry through a filter to form a filtrate; d) blending a reagent composition with the filtrate to form a soil mixture; and e) flowing the soil mixture through an analysis tool along a flow direction whereby a magnesium absorbance of the soil mixture is measured; and wherein soil mixture comprises a surfactant and the flow direction is substantially horizontal and orthogonal to the direction of gravity.

Embodiment 43. The method according to embodiment 42, wherein the liquid comprises water and the soil slurry of step b) is formed at a weight ratio of soil sample to liquid ranging from about 1:1 to about 1:5.

Embodiment 44. The method according to any one of embodiments 42 to 43, wherein the reagent composition includes a first reagent comprising tetrabutylammonium hydroxide and boric acid and a second reagent comprising chlorophosphonazo III.

Embodiment 45. The method according to embodiment 44, wherein the first reagent and the second reagent are present in a weight ratio of about 1:1.

Embodiment 46. The method according to any one of embodiments 42 to 45, wherein an extractant is blended with the soil slurry, the extractant comprising ammonium acetate.

Embodiment 47. The method according to any one of embodiments 42 to 46, wherein the surfactant is a non-ionic surfactant.

Embodiment 48. The method according to embodiment 47, wherein the non-ionic surfactant is selected from one or more of 4-nonylphenyl polyethylene glycol and poly(ethylene glycol)(18) tridecylether.

Embodiment 49. The method according to any one of embodiments 42 to 48, wherein the surfactant is substantially free of ionic compounds.

Embodiment 50. A method of analyzing calcium content in soil, the method comprising: a) obtaining a soil sample;

b) adding a liquid to the soil sample to form a soil slurry; c) flowing the soil slurry through a filter to form a filtrate; d) blending a reagent composition with the filtrate to form a soil mixture; and e) flowing the soil mixture through an analysis tool along a flow direction whereby a calcium absorbance of the soil mixture is measured; and wherein soil mixture comprises a surfactant and the flow direction is substantially horizontal and orthogonal to the direction of gravity.

Embodiment 51. The method according to embodiment 50, wherein the liquid comprises water and the soil slurry of step b) is formed at a weight ratio of soil sample to liquid ranging from about 1:1 to about 1:5.

Embodiment 52. The method according to any one of embodiments 50 to 51, wherein the reagent composition includes a first reagent comprising potassium hydrogen phthalate and a second reagent comprising chlorophosphonazo III.

Embodiment 53. The method according to embodiment 52, wherein the second reagent and the first reagent are present in a weight ratio of about 1:11.

Embodiment 54. The method according to any one of embodiments 50 to 53, wherein an extractant is blended with the soil slurry, the extractant comprising ammonium acetate.

Embodiment 55. The method according to any one of embodiments 50 to 54, wherein the surfactant is a non-ionic surfactant.

Embodiment 56. The method according to embodiment 55, wherein the non-ionic surfactant is selected from one or more of 4-nonylphenyl polyethylene glycol and poly(ethylene glycol)(18) tridecylether.

Embodiment 57. The method according to any one of embodiments 55 to 56, wherein the surfactant is substantially free of ionic compounds.

Embodiment 58. A method of analyzing phosphorus content in soil, the method comprising: a) obtaining a soil sample; b) adding a liquid to the soil sample to form a soil slurry; c) flowing the soil slurry through a filter to form a filtrate; d) blending a reagent composition with the filtrate to form a soil mixture; and e) flowing the soil mixture through an analysis tool along a flow direction whereby a phosphorus absorbance of the soil mixture is measured; wherein soil mixture comprises a surfactant and the flow direction is substantially horizontal and orthogonal to the direction of gravity.

Embodiment 59. The method according to embodiment 58, wherein the liquid comprises water and the soil slurry of step b) is formed at a weight ratio of soil sample to liquid ranging from about 1:2 to about 1:4.

Embodiment 60. The method according to any one of embodiments 58 to 59, wherein the reagent composition includes a first reagent comprising ammonium molybdate and sulfuric acid.

Embodiment 61. The method according to any one of embodiments 58 to 60, wherein an extractant is blended with the soil slurry, the extractant comprising selected from a first blend of HCl and ammonium fluoride and a second blend of acetic acid and aqueous ammonium fluoride Embodiment 62. The method according to any one of embodiments 58 to 61, wherein the surfactant comprises a non-ionic surfactant.

Embodiment 63. The method according to embodiment 62, wherein the non-ionic surfactant is selected from one or more of 4-nonylphenyl polyethylene glycol and poly(ethylene glycol)(18) tridecylether.

Embodiment 64. The method according to any one of embodiments 62 to 63, wherein the surfactant is substantially free of ionic compounds.

Embodiment 65. A method of analyzing pH in soil, the method comprising: a) obtaining a soil sample; b) adding a liquid to the soil sample to form a soil slurry; c) flowing the soil slurry through a filter to form a filtrate; d) blending an indicator composition with the filtrate to form a soil mixture; and e) flowing the soil mixture through an analysis tool along a flow direction whereby a pH value of the soil mixture is measured; and wherein the flow direction is oriented such that the soil mixture flows vertically.

Embodiment 66. The method according to embodiment 65, wherein the liquid comprises water and the soil slurry of step b) is formed at a weight ratio of soil sample to liquid ranging from about 1:2 to about 1:4.

Embodiment 67. The method according to any one of embodiments 65 to 66, wherein the indicator is selected from one of bromocresol green sodium salt, nitrazine yellow, chlorophenol red sodium salt, and phenol red sodium salt.

Embodiment 68. The method according to any one of embodiments 65 to 67, wherein an extractant is blended with the soil slurry, the extractant comprising calcium chloride.

Embodiment 69. The method according to any one of embodiments 65 to 68, the soil slurry of steps b) and c) and the soil mixture of step e) comprises a non-ionic surfactant.

Embodiment 70. The method according to embodiment 69, wherein the non-ionic surfactant is selected from 4-nonylphenyl polyethylene glycol and poly(ethylene glycol)(18) tridecylether.

Embodiment 71. The method according to any one of embodiments 65 to 68, the soil slurry of steps b) and c) and the soil mixture of step e) are substantially free of ionic surfactant.

Embodiment 72. The method according to any one of embodiments 65 to 68, the soil slurry of steps b) and c) and the soil mixture of step e) are substantially free of surfactant.

Embodiment 73. A method of analyzing pH in soil, the method comprising: a) obtaining a soil sample; b) adding a liquid to the soil sample to form a soil slurry; c) flowing the soil slurry through a filter to form a filtrate; d) blending an indicator composition with the filtrate to form a soil mixture; and e) flowing the soil mixture through an analysis tool along a flow direction whereby a pH value of the soil mixture is measured; and wherein soil mixture comprises a surfactant and the flow direction is substantially horizontal and orthogonal to the direction of gravity.

Embodiment 74. The method according to embodiment 73, wherein the liquid comprises water and the soil slurry of step b) is formed at a weight ratio of soil sample to liquid ranging from about 1:2 to about 1:4.

Embodiment 75. The method according to any one of embodiments 73 to 74, wherein the indicator is selected from one of bromocresol green sodium salt, nitrazine yellow, chlorophenol red sodium salt, and phenol red sodium salt.

Embodiment 76. The method according to any one of embodiments 73 to 75, wherein an extractant is blended with the soil slurry, the extractant comprises calcium chloride.

Embodiment 77. The method according to any one of embodiments 73 to 76, the soil slurry of steps b) and c) and the soil mixture of step e) comprises a non-ionic surfactant.

Embodiment 78. The method according to embodiment 77, wherein the non-ionic surfactant is selected from 4-nonylphenyl polyethylene glycol and poly(ethylene glycol)(18) tridecylether.

Embodiment 79. The method according to any one of embodiments 73 to 78, the soil slurry of steps b) and c) and the soil mixture of step e) are substantially free of ionic surfactant.

Embodiment 80. A method of analyzing buffer pH in soil, the method comprising: a) obtaining a soil sample; b) adding a liquid to the soil sample to form a soil slurry; c) flowing the soil slurry through a filter to form a filtrate; d) blending an indicator composition with the filtrate to form a soil mixture; and e) flowing the soil mixture through an analysis tool along a flow direction whereby a buffer pH value of the soil mixture is measured; and wherein the flow direction is oriented such that the soil mixture flows vertically.

Embodiment 81. The method according to embodiment 80, wherein the liquid comprises water and the soil slurry of step b) is formed at a weight ratio of soil sample to liquid ranging from about 1:2 to about 1:4.

Embodiment 82. The method according to any one of embodiments 80 to 81, wherein the indicator is selected from one of bromocresol green sodium salt, nitrazine yellow, chlorophenol red sodium salt, and phenol red sodium salt.

Embodiment 83. The method according to any one of embodiments 80 to 82, wherein an extractant is blended with the soil slurry, the extractant comprising Sikora buffer.

Embodiment 84. The method according to any one of embodiments 80 to 83, the soil slurry of steps b) and c) and the soil mixture of step e) comprises a non-ionic surfactant.

Embodiment 85. The method according to embodiment 84, wherein the non-ionic surfactant is selected from 4-nonylphenyl polyethylene glycol and poly(ethylene glycol)(18) tridecylether.

Embodiment 86. The method according to any one of embodiments 80 to 85, the soil slurry of steps b) and c) and the soil mixture of step e) are substantially free of ionic surfactant.

Embodiment 87. The method according to any one of embodiments 80 to 83, the soil slurry of steps b) and c) and the soil mixture of step e) are substantially free of surfactant.

Embodiment 88. A method of analyzing buffer pH in soil, the method comprising: a) obtaining a soil sample; b) adding a liquid to the soil sample to form a soil slurry; c) flowing the soil slurry through a filter to form a filtrate; d) blending an indicator composition with the filtrate to form a soil mixture; and e) flowing the soil mixture through an analysis tool along a flow direction whereby a pH value of the soil mixture is measured; and wherein soil mixture comprises a surfactant and the flow direction is substantially horizontal and orthogonal to the direction of gravity.

Embodiment 89. The method according to embodiment 88, wherein the liquid comprises water and the soil slurry of step b) is formed at a weight ratio of soil sample to liquid ranging from about 1:2 to about 1:4.

Embodiment 90. The method according to any one of embodiments 88 to 89, wherein the indicator is selected from one of bromocresol green sodium salt, nitrazine yellow, chlorophenol red sodium salt, and phenol red sodium salt.

Embodiment 91. The method according to any one of embodiments 88 to 90, wherein an extractant is blended with the soil slurry, the extractant comprising calcium chloride.

Embodiment 92. The method according to any one of embodiments 88 to 91, the soil slurry of steps b) and c) and the soil mixture of step e) comprises a non-ionic surfactant.

Embodiment 93. The method according to embodiment 92, wherein the non-ionic surfactant is selected from 4-nonylphenyl polyethylene glycol and poly(ethylene glycol)(18) tridecylether.

Embodiment 94. The method according to any one of embodiments 88 to 93, the soil slurry of steps b) and c) and the soil mixture of step e) are substantially free of ionic surfactant.

Embodiment 95. The method according to any one of embodiments 1 to 94, wherein the soil slurry of steps b) to d) is not subject to a centrifuge force.

Embodiment 96. The method according to any one of embodiments 1 to 95, wherein the soil mixture of steps e) is not subject to a centrifuge force.

The invention claimed is:

1. A method of analyzing pH in soil, the method comprising:
   a) obtaining a soil sample;
   b) adding a liquid to the soil sample to form a soil slurry;
   c) flowing the soil slurry through a filter to form a filtrate;
   d) blending an indicator composition with the filtrate to form a soil mixture; and
   e) flowing the soil mixture through an analysis tool along a flow direction whereby a pH value of the soil mixture is measured; and
   wherein soil mixture comprises a non-ionic surfactant and the flow direction is substantially horizontal and orthogonal to the direction of gravity.

2. The method according to claim 1, wherein the liquid comprises water and the soil slurry of step b) is formed at a weight ratio of soil sample to liquid ranging from about 1:2 to about 1:4.

3. The method according to claim 1, wherein the indicator composition comprises an indicator selected from one of bromocresol green sodium salt, nitrazine yellow, chlorophenol red sodium salt, and phenol red sodium salt.

4. The method according to claim 1, wherein an extractant is blended with the soil slurry.

5. The method according to claim 4, wherein the extractant comprises calcium chloride.

6. The method according to claim 4, wherein the extractant comprises potassium chloride, sodium chloride, or magnesium chloride.

7. The method according to claim 6, wherein the extractant comprises potassium chloride.

8. The method according to claim 6, wherein the extractant comprises magnesium chloride.

9. The method according to claim 6, wherein the extractant comprises sodium chloride.

10. The method according to claim 1, wherein the non-ionic surfactant comprises 4-nonylphenyl polyethylene glycol, poly(ethylene glycol)(18) tridecylether, or a combination thereof.

11. The method according to claim 1, wherein the surfactant is substantially free of ionic surfactants.

12. The method according to claim 1, wherein the soil slurry of steps b) to c) or the filtrate of step d) is not subject to a centrifuge force.

13. The method according to claim 12, wherein the soil mixture of steps step e) is not subject to a centrifuge force.

14. The method according to claim 1, wherein the indicator composition comprises bromocresol green and nitrazine yellow.

15. The method according to claim 14, wherein the bromocresol green and the nitrazine yellow are present in a weight ratio of the bromocresol green to the nitrazine yellow of 0.1:1 to 100:1.

16. The method according to claim 15, wherein the weight ratio of the bromocresol green to the nitrazine yellow is 0.2:1 to 20:1.

17. The method according to claim 14, wherein the bromocresol green is present in an amount of 0.01 to 0.08 wt. %, relative to the weight of the indicator composition.

18. The method according to claim 14, wherein the nitrazine yellow is present in an amount of 0.01 to about 0.1 wt. %, relative to the weight of the indicator composition.

19. A method of analyzing pH in soil, the method comprising:

a) obtaining a soil sample;

b) adding a liquid to the soil sample to form a soil slurry;

c) flowing the soil slurry through a filter to form a filtrate;

d) blending an indicator composition with the filtrate to form a soil mixture, the indicator composition comprising bromocresol green and nitrazine yellow in a weight ratio of the bromocresol green to the nitrazine yellow is 0.2:1 to 20:1; and e) flowing the soil mixture through an analysis tool along a flow direction whereby a pH value of the soil mixture is measured; and wherein soil mixture comprises a surfactant selected from the group consisting of non-ionic surfactants and is free of ionic surfactants, and the flow direction is substantially horizontal and orthogonal to the direction of gravity.

\* \* \* \* \*